US007927785B2

(12) United States Patent (10) Patent No.: US 7,927,785 B2
Milhem et al. (45) Date of Patent: Apr. 19, 2011

(54) METHODS FOR IN VITRO EXPANSION OF HEMATOPOIETIC STEM CELLS

(75) Inventors: Mohammed Milhem, Chicago, IL (US);
Nadim Mahmud, Chicago, IL (US);
Donald Lavelle, Park Ridge, IL (US);
Yogen Saunthararajah, Chicago, IL (US); Joseph De Simone, Chicago, IL (US); Ronald Hoffman, Chicago, IL (US)

(73) Assignee: The Board of Trustees of the University of Illinois, Urbana, IL (US)

( * ) Notice: Subject to any disclaimer, the term of this patent is extended or adjusted under 35 U.S.C. 154(b) by 252 days.

(21) Appl. No.: 11/128,128

(22) Filed: May 12, 2005

(65) Prior Publication Data

US 2005/0276793 A1 Dec. 15, 2005

Related U.S. Application Data

(63) Continuation of application No. PCT/US03/35767, filed on Nov. 10, 2003.

(60) Provisional application No. 60/426,757, filed on Nov. 15, 2002.

(51) Int. Cl.
*A01N 1/02* (2006.01)
*A61K 48/00* (2006.01)
(52) U.S. Cl. .............................. 435/2; 435/1.1; 424/93.1
(58) Field of Classification Search .................. None
See application file for complete search history.

(56) References Cited

U.S. PATENT DOCUMENTS

| | | | |
|---|---|---|---|
| 4,218,478 A | 8/1980 | Omura et al. | |
| 4,714,680 A | 12/1987 | Civin | |
| 5,061,620 A | 10/1991 | Tsukamoto et al. | |
| 5,409,825 A | 4/1995 | Hoffman et al. | |
| 5,599,703 A | 2/1997 | Davis et al. | |
| 5,599,705 A | 2/1997 | Cameron | |
| 5,665,557 A | 9/1997 | Murray et al. | |
| 5,728,581 A | 3/1998 | Schwartz et al. | |
| 5,811,301 A | 9/1998 | Cameron | |
| 5,861,315 A | 1/1999 | Nakahata | |
| 5,905,041 A | 5/1999 | Beug et al. | |
| 5,942,496 A | 8/1999 | Bonadio et al. | |
| 5,997,860 A | 12/1999 | Bauer et al. | |
| 6,068,987 A | 5/2000 | Dulski et al. | |
| 6,184,211 B1 | 2/2001 | Szyf | |
| 6,255,293 B1 | 7/2001 | Kimchi | |
| 6,326,198 B1 | 12/2001 | Emerson et al. | |
| 6,368,636 B1 | 4/2002 | McIntosh et al. | |
| 6,399,568 B1 | 6/2002 | Nishino et al. | |
| 2002/0132343 A1* | 9/2002 | Lum ............................ | 435/372 |
| 2002/0136709 A1* | 9/2002 | Zahner et al. .............. | 424/93.21 |
| 2003/0044978 A1 | 3/2003 | Young et al. | |

FOREIGN PATENT DOCUMENTS

| | | |
|---|---|---|
| WO | WO 95/03693 | 2/1995 |
| WO | WO 95/05843 | 3/1995 |
| WO | WO 95/08105 | 3/1995 |
| WO | WO 98/56938 | 12/1998 |

OTHER PUBLICATIONS

Abboud et al., "Hydrophobic Adsorption Chromatography of Colony-Stimulating Activities and Erythroid-Enhancing Activity from the Human Monocyte-Like Cell Line, GCT," Blood 58(6):1148-1154 (1981).
Akashi et al., "Transcriptional accessibility for genes of multiple tissues and hematopoietic lineages is hierarchically controlled during early hematopoiesis," Blood 101(2):383-390 (2003).
Antonsson et al., "Effect of 5-Azacytidine and Congeners on DNA Methylation and Expression of Deoxycytidine Kinase in the Human Lymphoid Cell Lines CCFR/CEM/0 and CCRF/CEM/dCk$^{-1}$," Cancer Research 47:3672-3678 (1987).
Bazil et al., "Apoptosis of Human Hematopoietic Progenitor Cells Induced by Crosslinking of Surface CD43, the Major Sialoglycoprotein of Leukocytes," Blood 88(2):502-511 (1995).
Berardi et al., "Functional Isolation and Characterization of Human Hematopoietic Stem Cells," Science 267(5194):104-108 (1995).
Bestor et al., "Cloning and Sequencing of a cDNA Encoding DNA Methyltransferase of Mouse Cells; The Carboxyl-terminal Domain of the Mammalian Enzymes is Related to Bacterial Restriction Methyltransferases," J. Mol. Biol 203(4):971-983 (1988).
Blau, "Regulating the Myogenic Regulators," Society for Experimental Biology, 9-18 (1992).
Brandeis et al., "Dynamics of DNA Methylation During Development," BioEssays 15(11):709-713 (1993).
Brandt et al., "Ex Vivo Expansion of Autologous Bond Marrow CD34$^+$ Cells with Porcine Microvascular Endothelial Cells Results in a Graft Capable of Rescuing Lethally Irradiated Baboons," Blood 94(1):106-113 (1999).
Clark et al., "High sensitivity mapping of methylated cytosines," Nucl. Acids Res. 22(15):2990-2997 (1994). Conneally et al., "Expansion in vitro of transplantable human cord blood stem cells demonstrated using a quantitative assay of their lympho-myeloid repopulating activity in nonobese diabetic-*scid/scid* mice," Proc. Natl. Acad. Sci. USA 94:9836-41 (1997).
Covey et al., "Differences in DNA Damage Produced by Incorporation of 5-Aza-2'-deoxycytidine or 5,6-Dihydro-5-azacytidine into DNA of Mammalian Cells," Cancer Research 46:5511-5517 (1986).
Craig et al., "Expression of Thy-1 on Human Hematopoietic Progenitor Cells," J. Exp. Med. 177:1331-42 (1993).
Cross et al., "The lineage commitment of haemopoietic progenitor cells," Curr. Opin. Genet. Dev. 5:609-613 (1997).
Danet at al., "Dissociation between stem cell phenotype and NOD/SCID repopulating activity in human peripheral blood CD34$^+$ cells after ex vivo expansion," Experimental Hematology 29:1465-1473 (2001).

(Continued)

*Primary Examiner* — James (Doug) Schultz
(74) *Attorney, Agent, or Firm* — Marshall, Gerstein & Borun LLP

(57) ABSTRACT

The invention relates to methods of obtaining compositions for generating multipotent hematopoietic stem progenitor cells comprising expansion of hematopoietic stem cells in the presence of HDACI and IDM. Methods of obtaining compositions enriched in hematopoietic megakaryocyte progenitor cells are also provided. Compositions enriched for stem cells and populations of cells obtained therefrom are also provided by the invention.

21 Claims, 8 Drawing Sheets

OTHER PUBLICATIONS

Dexter at al., "Stimulation of Differentiation and Proliferation of Haemoppoietic Cells In Vitro," J. Cell Phys. 82:461-473 (1973).

Dexter et al., "Conditions Controlling the Proliferation of Haemopoietic Stem Cells in Vitro," J. Cell Phys. 9:335-344 (1976).

Dozmorov et al., "Limiting dilution analysis: from frequencies to cellular interactions," Immunol. Today, 5:265-268 (1984).

Fauser et al., "Stimulatory Activity for Human Pluripotent Hemopoietic Progenitors Produced by a Human T-Lymphocyte Cell Line," Stem Cells 1:73-80 (1981).

Ghoshal et al., "Inhibitors of Histone Deacetylase and DNA Methyltransferase Synergistically Activate the Methylated Metallothionein I Promoter by Activating the Transcription Factor MTF-1 and Forming an Open Chromatin Structure," Mol Cell Biol, 22(23):8302-8319 (2002).

Gilboa et al., "Gene therapy for infectious diseases: the AIDS model," Trends in Genetics 10:139-144 (1994).

Golde et al., "Production of erythroid-potentiating activity by a human T-lymphoblast cell line," Proc. Natl. Acad. Sci (USA) 77(1):593-596 (1980).

Heike et al., "Ex vivo expansion of hematopoietic stem cells by cytokines," Biochim. Biophys. Acta, 1592:313-321 (2002).

Heldin et al., "Platelet-derived growth factor: mechanism of action and possible in vivo function," Cell Regulation 1:555-566 (1990).

Hu et al., "Multilineage gene expression precedes commitment in the hemopoietic system" Genes Dev., 11:774-785 (1997).

International Search Report from PCT/US03/35767 dated May 24, 2004.

Ivanova et al., "A Stem Cell Molecular Signature," Science 298:601-604 (2002).

Jones et al. "The Role of DNA Methylation in Mammalian Epigenetics," Science 293:1068-1071 (2001).

Jones, "Gene activation by 5-azacytidine," In: A Razin, H Cedar and AD Riggs, Editors, *DNA methylation: Biochemistry and Biological Significance*, Springer Verlag, New York pp. 165-187 (1984).

Kitazono, et al., "Histone deacetylase inhibitor FR901228 enhances adenovirus infection of hematopoietic cells," Blood 99(6):2248-2251 (2002).

Krause, "Regulation of hematopoietic stem cell fate," Oncogene, 21:3262-3269 (2002).

Kumar et al., "The DNA (cytosine-5) methyltransferases," Nucl. Acids Res. 22(1):1-10 (1994).

Kyoizumi et al., "Implantation and Maintenance of Functional Human Bone Marrow in SCID-hu Mice," Blood 79(7):1704-1711 (1992).

List, "New Approaches to the Treatment of Myelodysplasia," The Oncologist 7(1):39-49 (2002).

Lusis, "Purification and Characterization of a Human T-Lymphocyte-Derived Granulocyte-Macrophage Colony-Stimulating Factor," Blood 57(1):13-21 (1981).

Lyons et al., "Determination of lymphocyte division by flow cytometry," J. Immunol. Methods 171:131-7 (1994).

Momparler et al., "Pharmacological approach for optimization of the dose schedule of 5-Aza-2'-deoxycytidine (Decitabine) for the therapy of leukemia," Leukemia 11:175-180 (1997).

Morrison et al., "Regulatory Mechanisms in Stem Cell Biology," Cell, 88:287-298 (1997).

Murray et al., "Enrichment of Human Hematopoietic Stem Cell Activity in the $CD34^+$ $Thy-1^+$ $Lin^-$ Subpopulation From Mobilized Peripheral Blood," Blood 85(2):368-378 (1995).

Nicola, et al., "Separation of Functionally Distinct Human Granulocyte-Macrophage Colony-Stimulating Factors," Blood 54:614-627 (1979).

Okabe et al., "Large-Scale Preparation and Characterization of Human Colony-Stimulating Factor," J. Cell Phys. 110:43-49 (1982).

Raizis et al., "A Bisulfite Method of t-Methylcytosine Mapping That Minimizes Template Degradation," Anal. Biochem 226:161-166 (1995).

Razin et al., "DNA Methylation and Gene Expression," Microbiol. Rev. 55(3):451-458 (1991).

Reik et al., "Epigenetic Reprogramming in Mammalian Development," Science 293:1089-1093 (2001).

Sakashita et al., "Dynamic DNA methylation change in the CpG island region of *p15* during human myeloid development," J. Clin. Invest. 108(8):1195-1204 (2001).

Sanchez del Pino et al., "Properties of the yeast nuclear histone deacetylase," Biochem J., 303:723-729 (1994).

Santos et al., "Stemness: Transcriptional Profiling of Embryonic and Adult Stem Cells," Science 298:597-600 (2002).

Srour, "Proliferative history and hematopoietic function of ex vivo expanded human $CD34^+$ cells," Blood, 96(4)1609-1612 (2000).

Staunton et al., "The Arrangement of the Immunoglobulin-like Domains of ICAM-1 and the Binding Sites for LFA-1 and Rhinovirus," Cell 61:243-54 (1990).

Sutherland et al., "Differential Sensitivity of CD34 Epitopes to Cleavage by *Pasteurella haemolytica* Glycoprotease: Implications for Purification of CD34-positive Progenitor Cells," Exp. Hematol. 20(5):590-99 (1992).

Sutherland et al., "Functional characterization of individual human hematopoietic stem cells cultured at limiting dilution on supportive marrow stromal layers," Proc. Natl Acad. Sci. (USA) 87:3584-3588 (1990).

Szyf et al., "Cell Cycle-dependent Regulation of Eukaryotic DNA Methylase Level*," J. Biol. Chem. 260(15):8653-8656 (1985).

Szyf et al., "Growth Regulation of Mouse DNA Methyltransferase Gene Expression*," J. Biol. Chem. 266(16):10027-10030 (1991).

Travers, et al., "Human CD34+ Hematopoietic Progenitor Cells Hyperacetylate Core Histones in Response to Sodium Butyrate, but Not Trichostatin A," Exper. Cell Res. 280:149-158 (2002).

Xiong et al., "COBRA: a sensitive and quantitative DNA methylation assay," Nucl. Acids Res. 25(12):2532-4 (1997).

Yoshida et al., "Trichostatin A and trapoxin: novel chemical probes for the role of histone acetylation in chromatin structure and function," BioEssays, 17(5):423-430 (1995).

Zanjani et al., "Engraftment and Long-Term Expression of Human Fetal Hemopoietic Stem Cells in Sheep Following Transplantation in Utero," J. Clin. Invest. 89:1178-88 (1992).

Zhu et al., "Hematopoietic cytokines, transcription factors and lineage commitment," Oncogene 21:3295-3313 (2002).

Breems et al., "Frequency Analysis of Human Primitive Haematopoietic Stem Cell Subsets Using a Cobblestone Area Forming Cell Assay," Leukemia 8:1095-1104 (1994).

Kees et al., "Biochemical pharmacology and DNa methylation studies of arabinosyl 5-azacytidine and 5,6-dihydro-5-azacytidine in two human leukemia cell lines PER-145 and PER-163," Anti-Cancer Drugs 6:303-310 (1995).

Lefkovits et al., "Limiting dilution analysis of the cells of immune system I. The clonal basis of the immune response," Immunology Today 5(9):265-268 (1994).

Schwartsmann et al., "Decitabine (5-Aza-2'-deoxycytidine; DAC) plus daunorubicin as a first line treatment in patients with acute myeloid leukemia: preliminary observations," Leukemia 11(1):S28-S81 (1997).

Smith, "Retroviral Vector-Mediated Gene Transfer into Hematopoetic Cells: Prospects and Issues," J. Hematother 1:155-66 (1992).

Srour et al., "Animal Models for Human Hematopoiesis," J. Hematother 1:143-153 (1992).

Thibault et al., "A Phase II Study of 5-AZA-2' Deoxycytidine (Decitabine) in Hormone Independent Metastatic (D2) Prostate Cancer," Tumori, 84:57-89 (1998).

Willemze et al., "A randomized phase II study on the effects of 5-Aza-2'-deoxycytidine combined with either amsacrine or idarubicin in patients with relapsed acute leukemia: an EORTC Leukemia Cooperative Group phase II study (06893)," Leukemia 11(1);S24-S28 (1997).

Yisraeli et al., "Gene Methylation Patterns and Expression," In DNA methylation: Biochemistry and Biological significance, pp. 353-378 (1985).

Yoshida et al., "A Novel Tetracyclic Peptide, Trapoxin, Induces Phenotypic Change from Transformed to Normal in *sis*-Oncogene-transformed NIH3T3 Cells," Jap J. Cancer Res., 83(4):324-328 (1992).

* cited by examiner

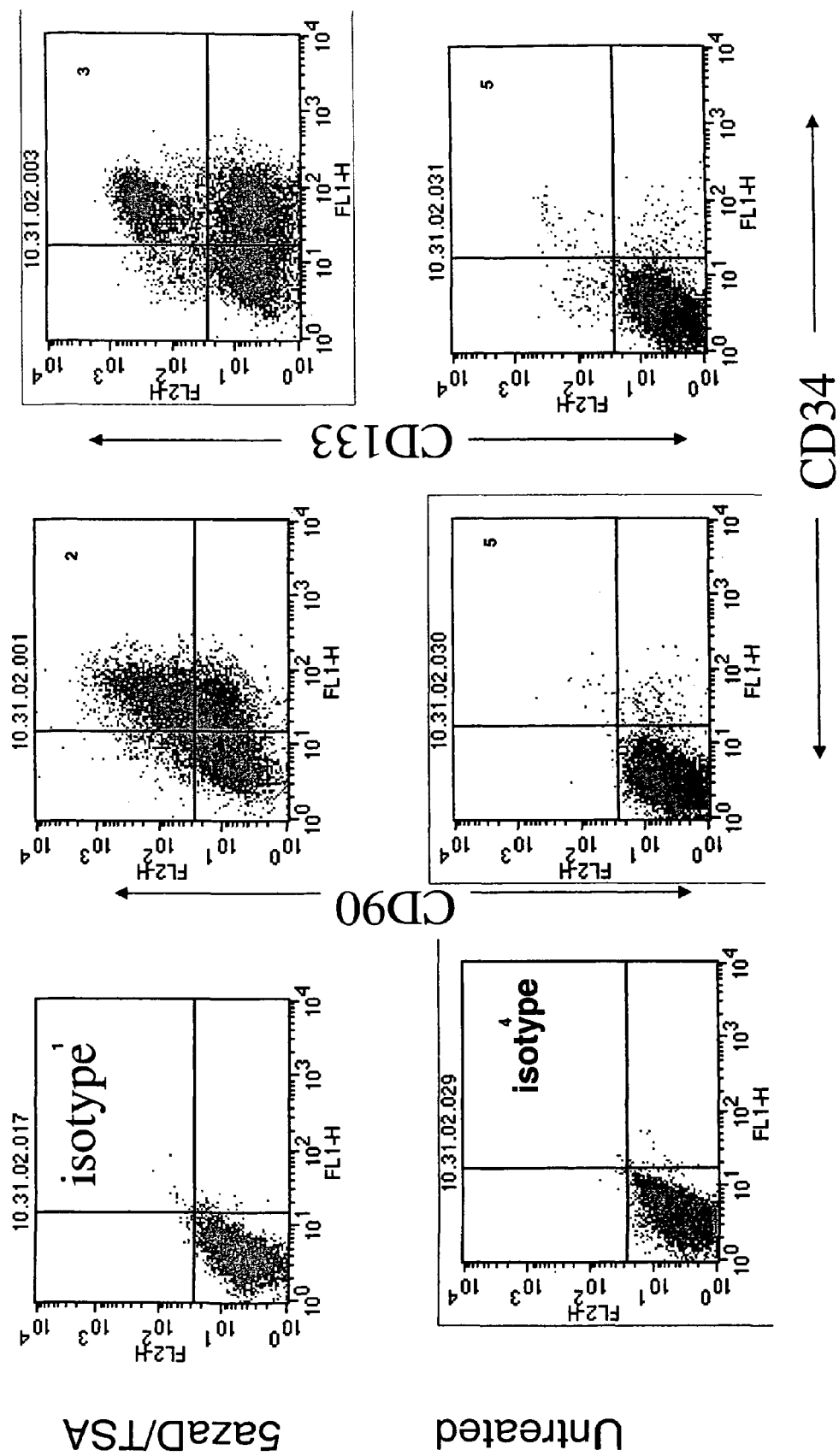
FIG. 2 Phenotypic Analysis of Marrow CD34+ Cells Following 9 Days of Culture

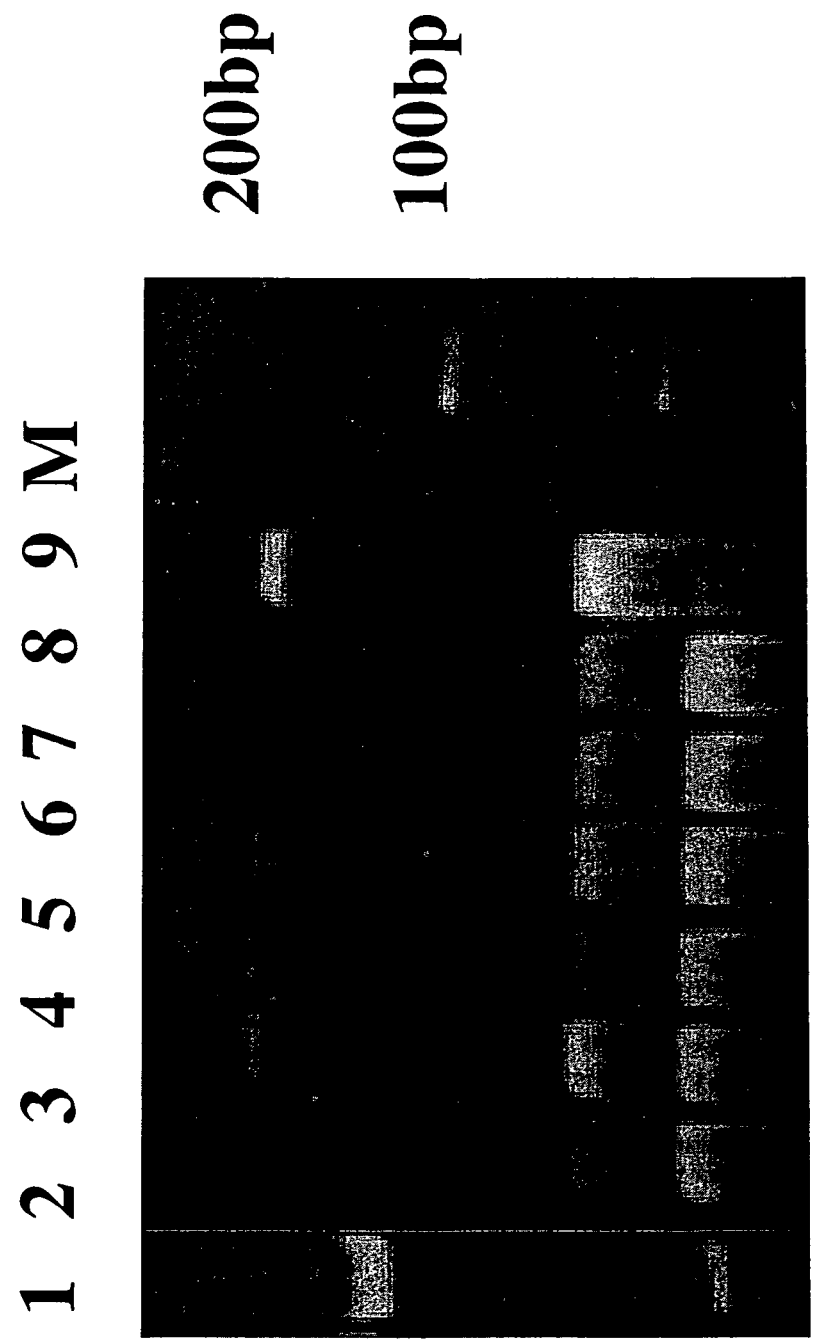
Fig. 3 COBRA Analysis of γ-globin Gene Methylation

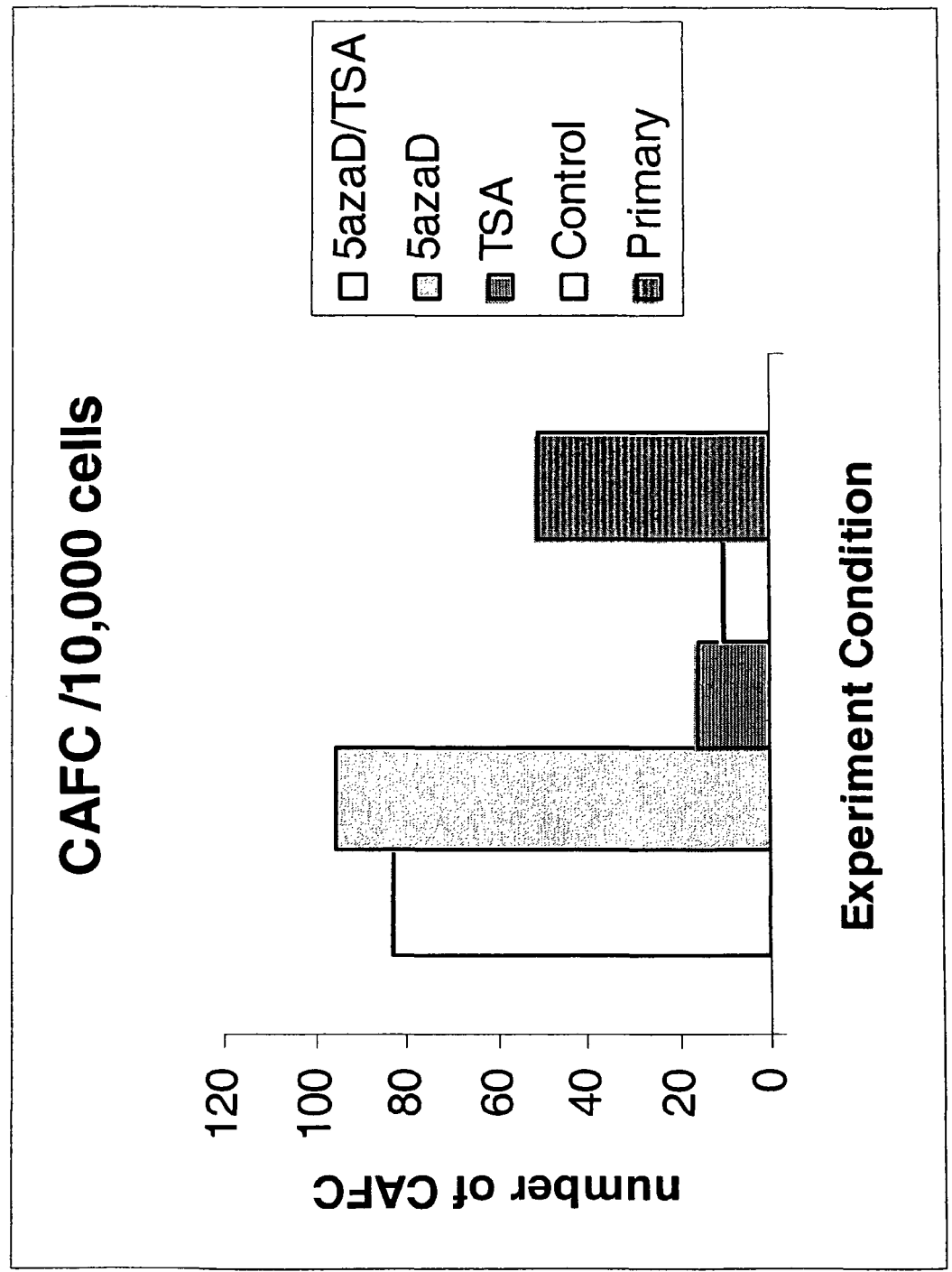
Fig. 4 Enriched CAFC with Cells Exposed to either to 5azaD or 5azaD & TSA in Combination After 9 days of Culture

METHODS FOR IN VITRO EXPANSION OF HEMATOPOIETIC STEM CELLS

The present application claims the benefit of priority under 35 U.S.C. §119 of U.S. Provisional Patent Application No. 60/426,757, which was filed Nov. 15, 2002 and is incorporated herein by reference in its entirety.

BACKGROUND

1. Field of the Invention

The present invention relates to expansion of human hematopoietic stem cells.

2. Background

The hematopoietic stem cell (HSC) is the progenitor cell for all blood cells. It is through the proliferation and differentiation, gives rise to the entire hematopoietic system. HSCs are believed to be capable of self-renewal—expanding their own population of stem cells—and they are pluripotent—capable of differentiating into any cell in the hematopoietic system. From this rare cell population, the entire mature hematopoietic system, comprising lymphocytes (B and T cells of the immune system) and myeloid cells (erythrocytes, megakaryocytes, granulocytes and macrophages) is formed. The lymphoid lineage, comprising B cells and T cells, provides for the production of antibodies, regulation of the cellular immune system, detection of foreign agents in the blood, detection of cells foreign to the host, and the like. The myeloid lineage, which includes monocytes, granulocytes, megakaryocytes as well as other cells, monitors for the presence of foreign bodies, provides protection against neoplastic cells, scavenges foreign materials, produces platelets, and the like. The erythroid lineage provides red blood cells, which act as oxygen carriers. As used herein, "stem cell" refers to hematopoietic stem cells and not stem cells of other cell types.

A schematic of hematopoiesis is shown in FIG. 8. This is a complex process which involves a hierarchy of HSC which can be influenced by a variety of external regulatory factors. Whether the fate of an individual HSC is determined by random or stochastic events or can actually be defined by external influences remains an important area of investigation. Morrison et al., Cell, 88:87-298, 1997; Krause, Oncogene, 21:3262-3269, 2002. To date attempts to create an in vitro environment which favors HSC self replication rather than commitment and differentiation has resulted in limited success Jiang et al., Oncogenes, 21:3295-3313, 2002; Guenahel et al., Exp. Hematol., 29:1465-1473, 2001; Srour, Blood, 96:1609-1612, 2000; Berardi et al., Science, 267:104-108, 1995; Heike et al., Biochim. Biophys. Acta, 1592:313-321, 2002.

Myelosuppression and myeloablation is often seen as a result of chemotherapy. Bone marrow transplantation, either autologous or allogeneic, can be used to replace a functional hematopoietic system. In addition, purified stem cells may be reinfused into the patient to restore hematopoiesis in these compromised patients. It also has been found that administration of chemotherapeutic agents and/or cytokines mobilizes bone marrow stem cells into the peripheral blood such that peripheral blood can be harvested as a source of stem cells. In an autologous transplant setting it is often particularly desirable to purify stem cells from the bone marrow or peripheral blood to use as a graft as a way of purifying long-term repopulating cells free of contaminating tumor cells. Tumor cells have been detected as high as 10% in mobilized peripheral blood collections and up to 80% in the mononuclear fraction from marrow.

Unlike whole bone marrow, stem cell replacement does not restore mature hematopoietic cells immediately. Due to the time necessary to generate mature cells from reinfused stem cells, there is a lag during which the patient remains immunocompromised. One proposed solution has been to expand the purified (and tumor-free) stem cells ex vivo to generate a cell population having both stem cells and slightly more differentiated cells, which would be able to provide both short- and long-term hematopoietic recovery.

Methods of bone marrow expansion have been developed, however, expansion of stem cells is not as straight-forward as expansion from a mature population. First, stem cells are very rare and, therefore, the number of stem cells isolated from any source will be very small. This reduces the size of the population that can be used to initiate the culture system. Second, the goal in stem cell expansion is not just to produce large quantities of mature cells, but also to retain stem cells and to produce many immature progenitor cells, which are capable of rapidly proliferating and replenishing mature cell types depleted in the patient. Upon reinfusion into a patient, the mature cells are cleared quickly whereas stem cells home to the marrow where long-term engraftment can occur (engraftment assays may be measured using for example, SCID mice using techniques well known to those of skill in the art). In addition, the immature progenitor cells can produce more cell types and more numbers of cells than the mature cells, thus providing short-term hematopoietic recovery. Stem cells are now regularly cultured on adherent monolayer of stromal cells, which supports the viability of stem and early progenitor cells ("Dexter culture"; see Dexter et al. (1976) J. Cell Phys. 9:335). For clinical use, it is preferable to utilize a more easily defined stromal-free culture system. U.S. Pat. No. 5,409,825 describes stroma-free stem cell expansion. U.S. Pat. Nos. 5,728,581, 5,665,557, 5,861,315, 5,997,860, 5,905,041, 6,326,198 each incorporated herein by reference in its entirety describe additional methods known to those of skill in the art for the expansion of stem cells in culture.

Despite the availability of numerous methods for in vitro expansion of HSCs in culture, these methods remain inadequate for the production of HSCs for transplantation that maintain self-renewal capacity and multipotency. This is may be due to these cells undergoing an epigenetically-mediated loss of gene function accompanied by DNA methylation of a gene's promoter and by histone deacetylation, thereby resulting in a loss of primitive HSC function. Although the molecular signature that defines an HSC has recently been described, the patterns of gene expression that lead to HSC self replication rather than commitment remain unknown (Santos et al., Science 298:597-600, 2002; Ivanova et al., Science, 298:601-604, 2002).

Primitive HSC are thought to maintain an open chromatin structure that permits access to the entire HSC developmental program while more differentiated cells along the hematopoietic hierarchy are thought to characteristically undergo a step-wise progression of epigenetic events that controls transcriptional events for each stage and class of progenitor cells (Akashi et al., Blood, 101:383-389, 2003). HSC promiscuously express a set of transcription factors that are restricted as the process of commitment to a particular pathway of differentiation occurs. Jiang et al., Oncogenes, 21:3295-3313, 2002; Akashi et al., Blood, 101:383-389, 2003; Hu et al., Genes Dev., 11:774-785, 1997). These events likely involve the activation and/or silencing of yet to be identified groups of pivotal genes that are influenced by a variety of epigenetic events.

In short, conditions previously utilized for in vitro stem cell expansion result in silencing of genes required for HSC to undergo symmetrical cell division. Accordingly, a need exists for methods and compositions for efficient culture and expansion of stem cells under controlled conditions that will yield suitable numbers of stem/progenitor cells for clinical use.

SUMMARY OF THE INVENTION

The present invention is directed to methods and compositions for efficient culture and expansion of stem cells under controlled conditions that will yield suitable numbers of stem/progenitor cells for clinical use. More particularly, it is demonstrated herein that the behavior of HSCs cells in vitro can be altered by the sequential addition of DNA methylation inhibitor and a histone deaceytlase inhibitor. Such pharmacologic agents not only result in the expansion of the numbers of cells expressing a primitive phenotype but also alters the differentiation program that leads to a persistent capacity to generate multipotent progenitors. Hence, compositions which alter HSC methylation and acetylation may be used to produce HSC populations for clinical use.

In particular embodiments, the present invention is directed to a method for the ex vivo expansion of multipotential hematopoietic cells, comprising culturing the cells in a medium comprising an inhibitor of DNA methylation (IDM) and a histone deacetylase inhibitor (HDACI), said IDM and HDACI being present in amounts effective to produce a composition substantially enriched in a subpopulation of hematopoietic stem cells as compared to expansion of said hematopoietic cells in the absence of said IDM and HDACI.

The cells to be expanded in the instant methods may be obtained from cord blood, peripheral blood, embryonic stem cells, or bone marrow. In certain embodiments, the multipotential hematopoietic cells are progenitor and/or stem cells obtained by CD34 selection. In other aspects, the multipotential hematopoietic cells are stem cells functionally selected by the removal of proliferating cells.

In preferred embodiments, the IDM is 5 aza 2'deoxycytidine, however, those of skill in the art will be aware of analogs derivative and other agents that may be used as inhibitors of DNA methylation. Any inhibitor of DNA methylation may be used in the present methods. In certain aspects, the IDM is used at a concentration of between about $10^{-3}$M to about $10^{-9}$M. Those of skill in the art will be able to adjust the concentrations of the IDM such that DNA methylation is inhibited. In preferred embodiments, the IDM is used at a concentration of about $10^{-6}$M.

The methods of the invention also use an HDACI, which is preferably added in a concentration of between about 1 ng/ml to about 100 ng/ml. Preferably, the HDACI is added in a concentration of between about 1 ng/nl and about 10 ng/ml. In specific embodiments, the HDACI is TSA.

The IDM is added to the culture prior to said HDACI. Alternatively, the IDM may be added to the culture after said HDACI. In still other embodiments, the IDM is added to the culture concurrently with said HDACI. In certain embodiments, the culture media may be changed prior to the addition of the second agent. In preferred embodiments, the DMI is added to the culture prior to the HDACI, and a time period is allowed to elapse before the addition of the HDACI. In specific embodiments, the HDACI ma be added 2, 3, 4, 5, 6, 7 or more days after the addition of the IDM. Thus, the time period for expansion of the cells may be in the order of days or weeks. The cells may be cultured on as small scale or may be produced in bioreactors. In specific embodiments, the culture medium comprises at least one cytokine selected from the group consisting of SCF, IL-3, GM-CSF, IL-6 and EPO. Of course these are only exemplary cytokines and other cytokines also may be used. Further it is contemplated that the culture media may comprise a cocktail of two, three, four, five, six or more cytokines. Such cytokines may include, but are not limited to stem cell factor, Interleukin-1 (IL-1), Interleukin-2 (IL-2), Interleukin-3 (IL-3), Interleukin-4 (IL-4), Interleukin-5 (IL-5), Interleukin-6 (IL-6), Interleukin-7 (IL-7), Interleukin-8 (IL-8), Interleukin-9 (IL-9), Interleukin-10 (IL-10), Interleukin-11 (IL-11), Interleukin-12 (IL-12), erythropoietin (FPO), Granulocyte Colony-stimulating Growth Factor (G-CSF), Macrophage Colony-Stimulating Factor (M-CSF), Granulocyte-Macrophage Colony-Stimulating Factor (GM-CSF), Insulin-like Growth Factor-1 (IGF-1), Flt-3 ligand, thrombopoietin (TPO), Leukemic Inhibitory Factor (LIF) and fibroblast growth factor (FGF) and bone morphogenic proteins. Those of skill in the art are aware of compositions that comprise these cytokines and factors that can be used in various growth media.

In particularly preferred embodiments, the present invention contemplates an expansion protocol in which the stem cells are initially grown in a cytokine cocktail that comprises IL-3, Flt-3, thrombopoeitin, and SCF. After a sufficient period of time in this initial cytokine cocktail, e.g., 48 hours, the media is changed to contain a cytokine cocktail that comprises Flt-3, thrombopoeitin, and SCF. The concentrations of each of these cytokines may vary from about 20 ng/mL to about 150 ng/mL. In other embodiments, the media is changed to contain a second medium that comprises IL-6, G-CSF, EPO, and SCF. The concentrations of each of these cytokines may vary from about 20 ng/mL to about 150 ng/mL. Those of skill in the art will be able to vary these concentrations and still remain within the teachings of the present invention.

It is contemplated that the growth of the hematopoietic stem cells in the presence of HDACI and IDM results in at least a 3-fold increase in CD34+CD90+ cells as compared to growth in the absence of said HDACI and IDM. Preferably, the growth of the hematopoietic stem cells in the presence of HDACI and IDM results in at least a 5-fold increase in CD34+ CD90+ cells as compared to growth in the absence of said HDACI and IDM. Other embodiments contemplated that the growth the hematopoietic stem cells in the presence of HDACI and IDM that results in at least a 7-fold increase in CD34+CD90+ cells as compared to growth in the absence of said HDACI and IDM. Still other methods produce a growth of said hematopoietic stem cells in the presence of HDACI and IDM results in at least a 10-fold increase in CD34+ CD90+ cells as compared to growth in the absence of said HDACI and IDM.

In the methods of the invention, the hematopoietic cells are separated from other cells by selecting for cells for expression of at least one marker associated with stem cells or by physical separation means. In specific embodiments, the marker is selected from the group consisting of CD34, Thy-1, a lineage-specific marker and rho123. The lineage specific marker may be any lineage specific marker, for example, it may be selected from the group consisting of CD2, CD14, CD15, CD16, CD19, and glycophorin A.

The present invention contemplates kits for use in the expansion of HSCs. In preferred embodiments kits are contemplated that comprise an IDM and an HDACI provided in individual containers or as a mixture in a single container in an amount effective for use in expansion of multipotential hematopoietic cells according to the methods described herein. Preferably, the kits may further comprise one or more cytokines.

The invention further contemplates isolated subpopulations of cells produced by the present expansion methods.

Such cells will be useful in a clinical setting for e.g., bone marrow transplantation and for any other clinical embodiment in which stem cells and/or progenitor cells are needed. Thus, preferred embodiments contemplated a subpopulation of cells obtained by the method in which the cells have been grown in a medium comprising an inhibitor of DNA methylation (IDM) and a histone deacetylase inhibitor (HDACI), said IDM and HDACI being present in amounts effective to produce a composition substantially enriched in a subpopulation of hematopoietic stem cells as compared to expansion of said hematopoietic cells in the absence of said IDM and HDACI. In particular embodiments, it is contemplated that prior to the expansion, said cells were stably transformed or transfected with a polynucleotide that encodes a therapeutic gene product in a manner allowing the expression of said therapeutic gene product in said cell. The therapeutic gene may be any gene that can be delievered for the purposes of gene therapy. Exemplary such genes include but are not limited to genes that encode α-globin, β-globin, γ-globin, cytokines, β-interferon, g-interferon, cytosine deaminase, adenosine deaminase, β-glucoronidase, p53, p16, p21, MMAC, p73, BRAC1, growth factors, hormones, SCID, Gamma-C, MDX, JAK-3 and CFTR and chemokines and the like. Also contemplated is a method of treating a patient by administering to the patient a composition that comprises the subpopulation of cells obtained above. In specific embodiments, the patient has undergone myeloablative therapy prior to administration of the cells.

Specifically contemplated herein is a method of repopulating mammalian bone marrow comprising obtaining a stem cells from a donor mammal; culturing said cells in a medium comprising an inhibitor of DNA methylation (IDM) and a histone deacetylase inhibitor (HDACI), said IDM and HDACI being present in amounts effective to produce a composition substantially enriched in a subpopulation of hematopoietic stem cells as compared to expansion of said hematopoietic cells in the absence of said IDM and HDACI; and introducing said cells into a host mammal. In donor and the host may, but need not be, the same subject. As used herein the term host is intended to mean recipient of the HSC-based therapy. Preferably, the host is a human host. In preferred embodiments, the donor also is human. In particular embodiments, it is contemplated that the HSC therapy of the present invention is given to an individual in need of such therapy. Such an individual may have been treated with a myeloablative therapy. For example, the individual may be a cancer patient undergoing chemo and/or radiotherapy. Thus the HSC compositions produced by the present invention will be useful in conjunctive therapy as a bone marrow transplant. Preferably, the HSC cells are reintroduced or introduced into the subject after the course of myeloablative therapy has been completed.

BRIEF DESCRIPTION OF THE DRAWINGS

The following figures form part of the present specification and are included to further illustrate aspects of the present invention. The invention may be better understood by reference to the drawings in combination with the detailed description of the specific embodiments presented herein.

FIG. 2. Phenotypic Analyses of Marrow $CD34^+$ Cells Following 9 days of Culture. This figure shows FACS (Fluorescence Activated Cell Sorter) analyses showing the phenotype of the cultured cells under 2 conditions. Upper half of this figure shows the experimental condition treated with 5azaD and TSA together. 1) isotype 2) $CD34^+CD90^+$ 3) $CD34^+CD133^+$. The lower half shows the phenotype untreated cells (control) after 9 days 4) isotype 5) $CD34^+CD90^+$ 6) $CD34^+CD133^+$.

FIG. 3. Cobra Anayslis of gamma-globin Gene Methylation. Marrow CD34+ cells were cultured for 5 days in different conditions and their hypomethylation status was analyzed using COBRA The identity of the lanes is as follows (1) Day 0 primary cells; (2) 1×10–6 M DAC; (3) 1×10–6 M DAC; TSA 5 ng/ml; (4) 1×10–8 M DAC; (5) 1×10–8 M DAC; TSA 5 ng/ml; (6) 1×10–7 M DAC; (7) 1×10–7 M DAC; TSA 5 ng/ml (8) Day 5 untreated (control); (9) $H_2O$ blank; (M) 100 bp DNA ladder.

FIG. 4 Enriched CAFC with Cells Exposed to either to 5azaD or 5azaD & TSA in Combination After 9 days of Culture FIG. 5. CFSE labeled cell division history of CD34+ CD90+ after 9 days of culture. Cell division history of CD34+ CD90+ after 5 and 9 days of culture labeled with CFSE. Each panel shows a representative flow cytometry profile for CFSE fluorescence intensity as a function of cell number for each day point studied. FIG. 4A) represents uncultured CD34+ cells; FIG. 4B) represents CD34+CD90+ cells after 5 days of culture; FIG. 4C) represents CD34+CD90+ cells after 9 days of culture. The number above each peak indicates the number of cell divisions undergone by cells within each peak of CFSE fluorescence.

FIG. 6A-C indicates the analysis of mice (n=1) that did not receive any human cell graft (negative control). FIG. 6D-F indicates the analysis of the marrow from mice (n=4) receiving cells exposed to cytokines alone. FIG. 6G-I indicates the analysis of the marrow from mice (n=3) receiving cells exposed to 5azaD and TSA. FIG. 6A) isotype negative control; FIG. 6B) CD19 PE and CD45 FITC negative control; FIG. 6C) CD34 PE and CD45 FITC negative control; FIG. 6D) isotype cytokines alone; FIG. 6E) CD19 PE and CD45 FITC cytokines alone; FIG. 6F) CD34 PE and CD45 FITC exposed to cytokines alone; FIG. 6G) isotype for exposed to 5azaD and TSA; FIG. 6H) CD 19PE and CD45 FITC of cells exposed to 5azaD and TSA; FIG. 6I) CD34 PE and CD45 FITC of exposed to 5azaD and TSA.

BRIEF DESCRIPTION OF THE TABLES

Figure 1:
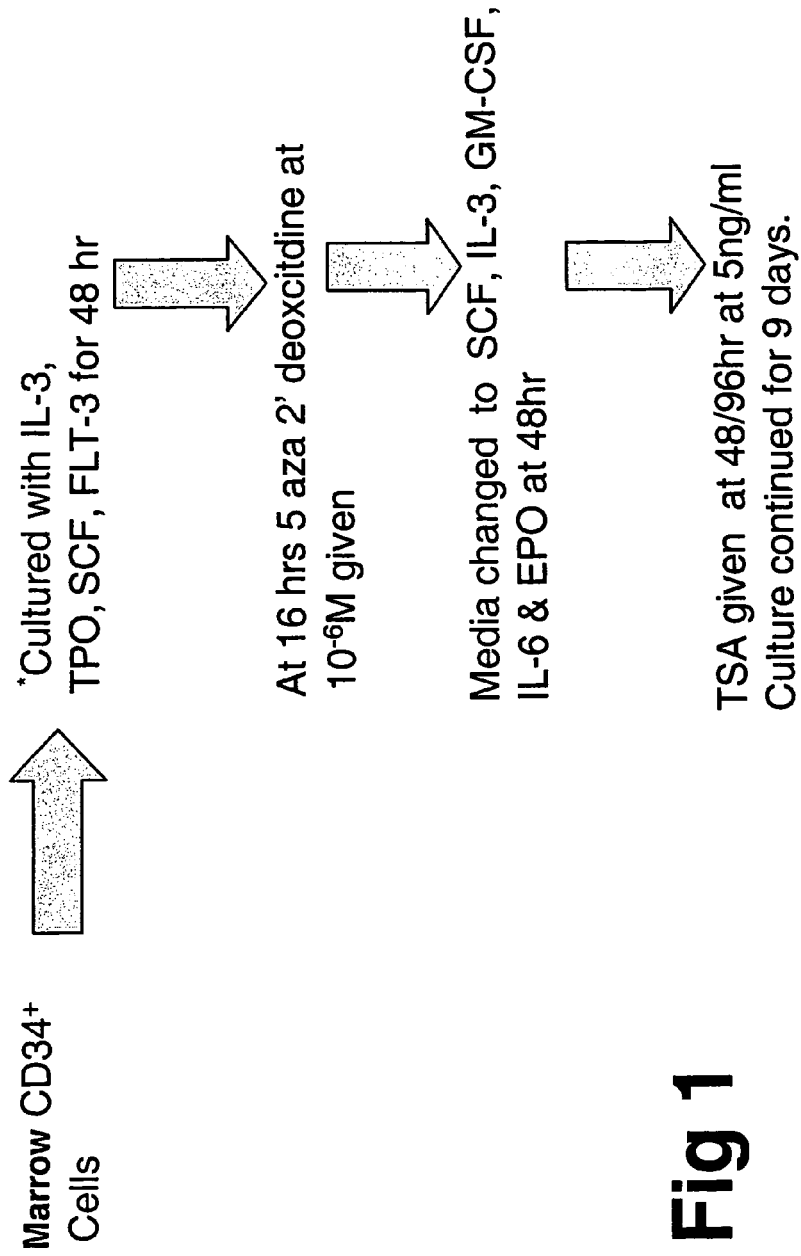
FIG. 1. Experimental Design for Expansion of HSC using the method of the present invention. This figure provides an outline of the different steps utilized in the method. Initial cytokines used include IL-3, TPO, SCF, FLT-3. At 48 hours this was switched to SCF, IL-3, EPO, GM-CSF and IL-6 (Differentiating Media). TSA was given after the 5azaD at 2 time points 48 h and 96 h. The culture media was changed first then the TSA was given. Doses of Drugs 5 aza 2' deoxycitidine at $10^{-6}$M, the TSA at 5-10 ng/ml. * Some of the data presented in the present application were derived from studies performed with differentiating media used for the nine days with very similar results.

The present specification includes tables 1-11 which form part of the present specification and are included to further illustrate aspects of the present invention. The invention may be better understood by reference to these tables in combination with the detailed description of the specific embodiments presented herein. The following description provides details of the information depicted in the tables.

Table 1. Maintenance of Primitive HSC *Phenotype After 9 Days of Culture. This table shows the phenotype of cells with regards to primitive markers in different experimental conditions after 9 days of culture. The primary cells reflect the starting phenotype of these cells on day 0. *The table shows data from averages pooled from multiple experiments as % of total cells. **Most of the cells that were CD34+ were lineage negative throughout all experimental conditions. # The 5-FU arm had very few cells due most likely to the cytotoxic activity of 5-FU.

Table 2. Expansion of the CD34+CD90+ Compartment After 9 days of Culture. This table shows the percentage of CD34+ and CD34+CD90+ cells and the absolute numbers with each experimental condition after 9 days of culture. There is a significant increase in the number of CD34+CD90+ cells with an overall maintenance of the total number of CD34+ cells in comparison to the primary cells. The starting cell counts were $1 \times 10^5$/well CD34+ cells (refer to table one for phenotype of primary cells). Counts are given/well.

Table 3. Marrow CD34+ cells cultured in presence of 5azaD and TSA retain CFC (colony forming cells) potential. This table shows the mean number of colonies obtained from 3 independent experiments . following 9 days of culture in different conditions 1000 unfractionated cells/plate (not selected for CD34+ cells) were placed in methylcellulose culture and enumerated on day 14 after initiation of cultures. Colonies included CFU-GM (colony forming Unit-granulo-monocytic), BFU-E (Burst Forming Unit-Erythroid), CFU-Mix (multipotential progenitor that gives rise to erythroid and granulocytic/monocytic colonies). Primary cells were plated on day 0 after being selected. Clonogenic potential was calculated as total colonies/number of cells plated×100.

Table 4. TSA Increases the Number of Cycling Cells. Cell cycle analysis at 48 h and 72 h from the start of the experiment is shown. Cells were examined by FACS analysis for cell cycle. $SG_2M$ % indicates cells in active DNA synthesis and indicates cells that may be actively cycling. This increased cycling allows the incorporation of the hypomethylating agent 5azaD.

Table 5. Quantitation of Hypomethylation of Marrow Cells following 5 days of culture. COBRA anaylsis was used as in FIG. 3. % of cells hypomethylated was approximated. Significant hypomethylation was seen with all combinations of drugs.

Table 6. Enrichment of the Frequency of CAFC Following Exposure of Cells to Either 5azaD or 5azaD & TSA in Combination After 9 Days of Culture. Cobblestone area forming cell (CAFC) assay in limiting dilution was performed using marrow CD34+ cells after 9 days of culture in order to determine the long term clonogenic potential. Cultures were counted for cobblestone areas after 5 weeks. This table shows number of CAFC/10,000 cells. Primary marrow CD34+ cells were plated on Day 0 whereas cells from day 9 culture were plated unfractionated (no CD34+ selection was done).

Table 7. The effect of drug treatment on methylation status on the −256th position of the γ-promtor region.

Table 8. Phenotype of CD34+ cells prior to and after exposure to 5 azaD and TSA. Each number represents the mean of 3 experiments±the standard error of the mean. *Lineage negative represents those cells that do not express phenotypic markers associated with terminally differentiated cells (CD 2, CD14, CD15, CD16, CD19 Glycophorin A). There is a significant increase in the percent of each marker CD90+ and CD 38− in the cytokines and sequential 5azaD and TSA treated culture when compared with the primary cells (P<0.01 and P<0.005 respectively, student paired t-test). There was no significant difference for CD 117+ and lineage markers.

Table 9. Effects of Drug Treatment on Numbers of Hematopoietic Progenitor Cells. Each number represents the mean of 3 experiments±the standard error of the mean. Fold change is calculated as the change in CD34+CD90+ cell numbers of the treated cells as compared to the primary cell numbers. There is a significant increase in the number of CD34+CD90+ cells between the cells exposed to sequential 5azaD and TSA and the cells exposed to cytokines alone (P<0.05, paired t-test).

Table 10. Ability of Epigenetically Modified Cells to Form Hematopoietic Colonies. Each number represents the mean of 2 experiments±the standard error of the mean. The plating efficiency is defined as total number of hematopoietic colonies/total cells plated×100. There is a significant increase in the total number of colonies when sequential addition of 5azaD and TSA are compared to cytokines alone (P<0.01).

Table 11. Hematopoeitic colonies cloned from NOD/SCID mouse marrow. This table shows the number of colonies after plating marrow cells from mice that received human grafts 7 weeks earlier. The estimated number of human colonies is determined by the percent of human cells that make up the pooled hematopoietic colonies from group of mice which stained positively with moAb against CD45/CD33 antibodies using FACS analysis multiplied by the total number of colonies enumerated.

DETAILED DESCRIPTION OF THE PREFERRED EMBODIMENTS OF THE INVENTION

Epigenetically mediated loss of gene function has been shown to be accompanied by DNA methylation of a gene's promoter and by histone deacetylation in the region containing the genes of interest. Conditions previously used for in vitro stem cell expansion cause silencing of genes required for HSC to undergo symmetrical cell division.

As described in further detail herein below, expansion of HSC in the presence of agents that inhibit DNA methylation and histone deacetylase activity promotes reprogramming of hematopoietic stem cells in vitro. Methods and compositions for resetting the developmental and transcriptional program of an adult HSC to change its fate through epigenetic mechanisms of hypomethylation and acetylation are contemplated by the present invention.

The invention relates to methods of obtaining compositions for generating multipotent hematopoietic stem progenitor cells comprising expansion of hematopoietic stem cells in the presence of HDACI and IDM. Methods of obtaining compositions enriched in hematopoietic megakaryocyte progenitor cells are also provided. Compositions enriched for stem cells and populations of cells obtained therefrom are also provided by the invention. It is contemplated that the HSCs and the enriched populations of cells obtained therefrom may be used in all therapeutic uses for which HSC are presently employed. For example, such compositions may be used in bone marrow transplants. The cells used in such a manner may be wild-type cells or may be cells which have been transformed/transfected with appropriate genetic constructs for the purposes of gene therapy. Therapeutic methods using HSCs are well known to those of skill in the art (e.g., see U.S. Pat. No. 6,368,636).

Compositions for Use in Reprogramming Hematopoietic Stem Cells In Vitro

The present invention employs compositions that alter HSC methylation and acetylation in order to reprogram HSC cells and mitigate gene silencing that disrupts symmetrical cell division of HSC during in vitro HSC expansion. The present section provides a brief discussion of DNA methylation inhibitors and histone deacetylase inhibitors that may be used for the methods described herein. The methods and compositions described in the patents recited below for producing and identifying inhibitors of HDACI and IDM may be adapted to identify additional compounds that will be useful in the present invention.

In the cultures conditions of the present invention, which may employ various cytokine combinations, varying amounts of IDM and HDACI may be added. The IDM and HDACI may be added concurrently at the beginning of the cell culture. Alternatively either the IDM or the HDACI agent may be added first and the other agent may be added later. For example, in preferred embodiments, the HDACI was added 80 hours after the initial exposure of the cells to IDM, a strategy which resulted in a 7 fold increase in CD34+CD90+ cells (22,000-160,000). Those of skill in the art will be able to modify the time of exposure to the two types of agent, the amount of agent to be added and the order in which the agents are added to optimize HSC expansion. Of course, it should be understood that use of either the IDM or the HDACI alone in the HSC expansion culture also may be beneficial in producing an increase in HSC expansion and improving the reprogramming of hematopoietic cells.

a. Inhibitors of DNA Methylation

DNA methylation is a postreplicative covalent modification of DNA that is catalyzed by the DNA methyltransferase enzyme (MeTase) (Koomar et al., 1994, Nucl. Acids Res. 22:1-10; and Bestor et al., 1988, J. Mol. Biol. 203:971-983). In vertebrates, the cytosine moiety at a fraction of the CpG sequences is methylated (60-80%) in a nonrandom manner generating a pattern of methylation that is gene and tissue specific (Yisraeli and M. Szyf, 1985, In DNA methylation: Biochemistry and Biological significance, pp. 353-378, Razin et al., (Ed), Springer-Verlag, N.Y.). It is generally believed that methylation in regulatory regions of a gene is correlated with a repressed state of the gene (Yisraeli and Szyf, 1985, In DNA methylation: Biochemistry and Biological significance, pp. 353-378, Razin et al., (Ed), Springer-Verlag, N.Y.; and Razin et al., 1991, Microbiol. Rev. 55:451-458). DNA methylation can repress gene expression directly, by inhibiting binding of transcription factors to regulatory sequences or indirectly, by signaling the binding of methylated-DNA binding factors that direct repression of gene activity (Razin et al., 1991, Microbiol. Rev. 55:451-458).

It is well established that regulated changes in the pattern of DNA methylation occur during development and cellular differentiation (Razin et al., 1991, Microbiol. Rev. 55:451-458; and Brandeis et al., 1993, Bioessays 13:709-713). The pattern of methylation is maintained by the DNA MeTase at the time of replication and the level of DNA MeTase activity and gene expression is regulated with the growth state of different primary (Szyf et al., 1985, J. Biol. Chem. 260:8653-8656) and immortal cell lines (Szyf et al., 1991, J. Bol. Chem. 266:10027-10030). This regulated expression of DNA MeTase has been suggested to be critical for preserving the pattern of methylation. It is the inhibition of such DNA methylation in cultures of HSC that is useful in the methods of the present invention.

Methods and compositions for inhibiting DNA methylation are well known to those of skill in the art. Such methods are disclosed in for example U.S. Pat. No. 6,184,211, which is incorporated herein by reference in its entirety and describes a reduction of the level of DNA methylation through inhibitors and antagonists in order to inhibit the excessive activity or hypermethylation of DNA methyltransferase in cancer cells to induce the original cellular tumor suppressing program, to turn on alternative gene expression programs, to provide therapeutics directed at a nodal point of regulation of genetic information, and to modulate the general level of methylase and demethylase enzymatic activity of a cell to permit specific changes in the methylation pattern of a cell. Such methods and compositions may be used in the present invention to promote expansion of HSC in culture.

U.S. Pat. No. 6,255,293 is specifically incorporated herein by reference as providing a teaching of demethylation of cells using methods and compositions relating to demethylating agents such as 5-aza-2'-deoxycytidine. Use of such a compound as the demethylation compound is particularly useful in the present invention as protocols of 5-aza-2'-deoxycytidine treatment of patients were approved in the past and further used in the USA for other purposes, such as for use as an anticancer drug which induces cellular differentiation and enhanced expression of genes involved in tumor suppression, immunogenicity and programmed cell death. Thus, the use of 5-aza-2'-deoxycytidine and derivatives and analogs thereof in the HSC expansion methods of the present invention is specifically contemplated. It has been recognized that administration of this compound blocks DNA methylation. See, for example, Thibault et al, (1998), Momparler et al, (1997), Schwartsmann et al., (1997), Willemze et al, (1997) and Momparler, (1997), Reik et al., (2001), Blau, (1992), Jones et al., 2001.

Other agents for causing demethylation of methylated DNA or for preventing methylation of DNA also may be used in addition to or in combination with 5-aza-2'-deoxycytidine include but are not limited to 5,6-dihydro-5-azacytidine, 5-azacytidine, and 1-β-D-arabinofuranosyl-5-azacytidine. See Antonsson et al. (1987), Covey et al. (1986), and Kees et al. (1995). Any compound known to be a cytosine specific DNA methyltransferase inhibitor would be expected to be operable in the present invention. Any such compound can be readily tested without undue experimentation in order to determine whether or not it works in the context of the present invention in the same manner as 5-aza-2'-deoxycytidine, for example by repeating the experiments of the present examples with each proposed demethylating agent.

b. Histone Deactylase Inhibitors

Histone deacetylase and histone acetyltransferase together control the net level of acetylation of histones. Inhibition of the action of histone deacetylase results in the accumulation of hyperacetylated histones, which in turn is implicated in a variety of cellular responses, including altered gene expression, cell differentiation and cell-cycle arrest. Recently, trichostatin A and trapoxin A have been reported as reversible and irreversible inhibitors, respectively, of mammalian histone deacetylase (see e.g., Yoshida et al, Bioassays, 1995, 17(5):423-430). Trichostatin A has also been reported to inhibit partially purified yeast histone deacetylase (Sanchez del Pino et al, Biochem. J., 1994, 303:723-729).

In the present invention, Trichostatatin A is used as an HDACI. Trichostatin A is an antifungal antibiotic and has been shown to have anti-trichomonal activity as well as cell differentiating activity in murine erythroleukemia cells, and the ability to induce phenotypic reversion in sis-transformed fibroblast cells (see e.g. U.S. Pat. No. 4,218,478; Yoshida et al, Bioassays, 1995, 17(5):423-430 and references cited therein). Alternatively, Trapoxin A, a cyclic tetrapeptide, which induces morphological reversion of v-sis-transformed NIH3T3 cells may be used in the present invention as the HDACI (Yoshida and Sugita, Jap. J. Cancer Res., 1992, 83(4): 324-328).

Other HDACI compounds are well known to those of skill in the art. For example, U.S. Pat. No. 6,068,987, specifically incorporated herein by reference describes a number of cyclic tetrapeptides structurally related to trapoxin A as inhibitors of histone deacetylase. Depsipeptide is another agent that has commonly been used as an HDACI (Ghoshal et al., Mol Cell Biol., 22(23):8302-19, 2002). U.S. Pat. No. 6,399,568, incorporated herein by reference in its entirety, describes additional cyclic tetrapeptide derivatives that may be used as useful HDACI compounds in the HSC expansion methods of the present invention.

Methods of HSC Expansion

The present invention provides a method of expanding a population of cells substantially enriched in hematopoietic stem cells by culturing the cells in the presence of an IDM and an HDACI. The hematopoietic stem cells used in the expansion method may be substantially free of stromal cells. The method may be performed in closed, perfusable, culture containers or may be performed in an open culture system. A "closed culture" is one which allows for the necessary cell distribution, introduction of nutrients and oxygen, removal of waste metabolic products, optional recycling of hematopoietic cells and harvesting of hematopoietic cells without exposing the culture to the external environment, and does not require manual feeding or manual manipulation before the cells are harvested.

As used herein, "stem cells" refers to animal, especially mammalian, preferably human, hematopoietic stem cells and not stem cells of other cell types. "Stem cells" also refers to a population of hematopoietic cells having all of the long-term engrafting potential in vivo. Animal models for long-term engrafting potential of candidate human hematopoietic stem cell populations include the SCID-hu bone model (Kyoizumi et al. (1992) Blood 79:1 704; Murray et al. (1995) Blood 85(2) 368-378) and the in utero sheep model (Zanjani et al. (1992) J. Clin. Invest. 89:1179). For a review of animal models of human hematopoiesis, see Srour et al. (1992) J. Hematother. 1:143-153 and the references cited therein. At present, in vitro measurement of stem cells is achieved through the long-term culture-initiating cell (LTCIC) assay, which is based on a limiting dilution analysis of the number of clonogenic cells produced in a stromal co-culture after 5-8 weeks. Sutherland et al. (1990) Proc. Nat'l Acad. Sci. 87:3584-3588. The LTCIC assay has been shown to correlate with another commonly used stem cell assay, the cobblestone area forming cell (CAFC) assay, and with long-term engrafting potential in vivo. Breems et al. (1994) Leukemia 8:1095.

The stem cell population used in the present invention is preferably an enriched stem cell population, in order to maximize the content of stem and early progenitor cells in the expanded cell population. An example of an enriched stem cell population is a population of cells selected by expression of the CD34 marker. In LTCIC assays, a population enriched in $CD34^+$ cells generally have an LTCIC frequency in the range of $\frac{1}{50}$ to $\frac{1}{500}$, more usually in the range of $\frac{1}{50}$ to $\frac{1}{200}$. Preferably, the stem cell population will be more highly enriched for stem cells than that provided by a population selected on the basis of $CD34^+$ expression alone. By use of various techniques described more fully below, a highly enriched stem cell population may be obtained. A highly enriched stem cell population will typically have an LTCIC frequency in the range of $\frac{1}{5}$ to $\frac{1}{100}$, more usually in the range of $\frac{1}{10}$ to $\frac{1}{50}$. Preferably it will have an LTCIC frequency of at least $\frac{1}{50}$. Exemplary of a highly enriched stem cell population is a population having the $CD34^+/Thy-1^+/LIN^-$ phenotype as described in U.S. Pat. No. 5,061,620. A population of this phenotype will typically have an average LTCIC frequency of approximately $\frac{1}{20}$. Murray et al. (1995) supra; Lansdorp et al. (1993) J. Exp. Med. 177:1331. It will be appreciated by those of skill in the art that the enrichment provided in any stem cell population will be dependent both on the selection criteria used as well as the purity achieved by the given selection techniques.

As used herein, the term "expansion" is intended to mean an increase in cell number from the pluripotent stem cells used to initiate the culture. "Substantially free of stromal cells" shall mean a cell population which, when placed in a culture system as described herein, does not form an adherent cell layer.

The hematopoietic stem cells used to inoculate the cell culture may be derived from any source including bone marrow, both adult and fetal, cytokine or chemotherapy mobilized peripheral blood, fetal liver, bone marrow, umbilical cord blood, embryonic yolk sac, fetal liver, and spleen, both adult and fetal. In preferred embodiments, the hematopoietic stem cells are adult human bone marrow $CD34^+$ cells. Bone marrow cells may be obtained from any known source, including but not limited to, ilium (e.g. from the hip bone via the iliac crest), sternum, tibiae, femora, spine, or other bone cavities.

For isolation of bone marrow from fetal bone or other bone source, an appropriate solution may be used to flush the bone, including but not limited to, salt solution, conveniently supplemented with fetal calf serum (FCS) or other naturally occurring factors, in conjunction with an acceptable buffer at low concentration, generally from about 5-25 mM. Convenient buffers include, but are not limited to, Hepes, phosphate buffers and lactate buffers. Otherwise, bone marrow may be aspirated from the bone in accordance with conventional techniques.

In those embodiments in which the HSCs are being expanded for autologous bone marrow transplantation, it is preferable that the initial inoculation population of HSCs is separated from any neoplastic cells prior to culture. Isolation of the phenotype ($CD34^+$ $Thy-1^+$ $CD14^-CD15^-$) from multiple myeloma patients has been shown to reduce the tumor burden to less than 1 tumor cell per $10^5$ purified cells.

Selection of stem cells can be performed by any number of methods, including cell sorters, magnetic separation using antibody-coated magnetic beads, packed columns; affinity chromatography; cytotoxic agents joined to a monoclonal antibody or used in conjunction with a monoclonal antibody, including but not limited to, complement and cytotoxins; and "panning" with antibody attached to a solid matrix, e.g., plate, or any other convenient technique.

The use of separation techniques include, but are not limited to, those based on differences in physical (density gradient centrifugation and counter-flow centrifugal elutriation), cell surface (lectin and antibody affinity), and vital staining properties (mitochondria-binding dye rho123 and DNA-binding dye Hoechst 33342). Techniques providing accurate separation include but are not limited to, FACS, which can have varying degrees of sophistication, e.g., a plurality of color channels, low angle and obtuse light scattering detecting channels, impedance channels, etc.

The antibodies can be conjugated to identifiable agents including, but not limited to, enzymes, magnetic beads, colloidal magnetic beads, haptens, fluorochromes, metal compounds, radioactive compounds, drugs or haptens. The enzymes that can be conjugated to the antibodies include, but are not limited to, alkaline phosphatase, peroxidase, urease and .beta.-galactosidase. The fluorochromes that can be conjugated to the antibodies include, but are not limited to, fluorescein isothiocyanate, tetramethylrhodamine isothiocyanate, phycoerythrin, allophycocyanins and Texas Red. For additional fluorochromes that can be conjugated to antibodies, see Haugland, Molecular Probes: Handbook of Fluorescent Probes and Research Chemicals (1992-1994). The metal compounds that can be conjugated to the antibodies include, but are not limited to, ferritin, colloidal gold, and particularly, colloidal superparamagnetic beads. The haptens that can be conjugated to the antibodies include, but are not limited to, biotin, digoxygenin, oxazalone, and nitrophenol. The radioactive compounds that can be conjugated or incorporated into the antibodies are known to the art, and include but are not limited to technetium 99 m ($^{99}TC$), $^{125}I$ and amino acids comprising any radionuclides, including, but not limited to, $^{14}C$, $^{3}H$ and $^{35}S$.

Other techniques for positive selection may be employed, which permit accurate separation, such as affinity columns, and the like. The method should permit the removal to a residual amount of less than about 20%, preferably less than about 5%, of the non-target cell populations.

Cells may be selected based on light-scatter properties as well as their expression of various cell surface antigens. The purified stem cells have low side scatter and low to medium forward scatter profiles by FACS analysis. Cytospin preparations show the enriched stem cells to have a size between mature lymphoid cells and mature granulocytes.

It also is possible to enrich the inoculation population for CD34+ cells prior to culture, using for example, the method of Sutherland et al. (1992) Exp. Hematol. 20:590 and that described in U.S. Pat. No. 4,714,680. Preferably, the cells are subject to negative selection to remove those cells that express lineage specific markers. Methods of negative selection are known in the art. As used herein, lineage-negative (LIN−) refers to cells lacking at least one marker associated with lineage committed cells, e.g., markers associated with T cells (such as CD2, 3, 4 and 8), B cells (such as CD10, 19 and 20), myeloid cells (such as CD14, 15, 16 and 33), natural killer ("NK") cells (such as CD2, 16 and 56), RBC (such as glycophorin A), megakaryocytes (CD41), mast cells, eosinophils or basophils or other markers such as CD38, CD71, and HLA-DR. Preferably the lineage specific markers include, but are not limited to, at least one of CD2, CD14, CD15, CD16, CD19, CD20, CD33, CD38, HLA-DR and CD71. More preferably, LIN− will include at least CD14 and CD15. Further purification can be achieved by positive selection for, e.g., c-kit+ or Thy-1+. Further enrichment can be obtained by use of the mitochondrial binding dye rhodamine 123 and selection for rhodamine+ cells, by methods known in the art. A highly enriched composition can be obtained by selective isolation of cells that are CD34+, preferably CD34+LIN−, and most preferably, CD34+ Thy-1+ LIN−. Populations highly enriched in stem cells and methods for obtaining them are well known to those of skill in the art, see e.g., methods described in PCT/US94/09760; PCT/US94/08574 and PCT/US94/10501.

Selection of the stem cells need not be achieved solely with a marker specific for the cells. By using a combination of negative selection and positive selection, enriched cell populations can be obtained.

Various techniques may be employed to separate the cells by initially removing cells of dedicated lineage. Monoclonal antibodies are particularly useful for identifying markers associated with particular cell lineages and/or stages of differentiation. The antibodies may be attached to a solid support to allow for crude separation. The separation techniques employed should maximize the retention of viability of the fraction to be collected. Various techniques of different efficacy may be employed to obtain "relatively crude" separations. Such separations are where up to 10%, usually not more than about 5%, preferably not more than about 1%, of the total cells present are undesired cells that remain with the cell population to be retained. The particular technique employed will depend upon efficiency of separation, associated cytotoxicity, ease and speed of performance, and necessity for sophisticated equipment and/or technical skill.

The expansion method of the invention generally requires inoculating the population of cells substantially enriched in hematopoietic stem cells and substantially free of stromal cells into an expansion container and in a volume of a suitable medium such that the cell density is from at least about 5,000, preferably 7,000 to about 200,000 cells/mL of medium, and more preferably from about 10,000 to about 150,000 cells/mL of medium, and at an initial oxygen concentration of from about 2 to 20% and preferably less than 8%. In one embodiment, the initial oxygen concentration is in a range from about 4% to about 6%. In one aspect, the inoculating population of cells is derived from adult bone marrow and is from about 7,000 cells/mL to about 20,000 cells/mL and preferably about 20,000 cell/mL. In a separate aspect, the inoculation population of cells is derived from mobilized peripheral blood and is from about 20,000 cells/mL to about 50,000 cells/mL, preferably 50,000 cells/mL.

Any suitable expansion container, flask, or appropriate tube such as a 24 well plate, 12.5 cm² T flask or gas-permeable bag can be used in the method of this invention. Such culture-containers are commercially available from Falcon, Corning or Costor. As used herein, "expansion container" also is intended to include any chamber or container for expanding cells whether or not free standing or incorporated into an expansion apparatus such as the bioreactors described herein. In one embodiment, the expansion container is a reduced volume space of the chamber which is formed by a depressed surface and a plane in which a remaining cell support surface is orientated.

Various media can be used for the expansion of the stem cells. Illustrative media include Dulbecco's MEM, IMDM and RPMI-1640 that can be supplemented with a variety of different nutrients, growth factors, cytokines, etc. The media can be serum free or supplemented with suitable amounts of serum such as fetal calf serum or autologous serum. Preferably, if the expanded cells or cellular products are to be used in human therapy, the medium is serum-free or supplemented with autologous serum. One suitable medium is one containing IMDM, effective amounts of at least one of a peptone, a protease inhibitor and a pituitary extract and effective amounts of at least one of human serum albumin or plasma protein fraction, heparin, a reducing agent, insulin, transferrin and ethanolamine. In a further embodiment, the suitable expansion medium contains at least IMDM and 1-15% fetal bovine serum. Other suitable media formulations are well known to those of skill in the art, see for example, U.S. Pat. No. 5,728,581.

Regardless of the specific medium being used in any given the HSC expansion, the medium used is preferably supplemented with at least one cytokine at a concentration from about 0.1 ng/mL to about 500 ng mL, more usually 10 ng/mL to 100 ng/mL. Suitable cytokines, include but are not limited to, c-kit ligand (KL) (also called steel factor (StI), mast cell growth factor (MGF), and stem cell factor (SCF)), IL-6, G-CSF, IL-3, GM-CSF, IL-1α, IL-11 MIP-1α, LIF, c-mpl ligand/TPO, and flk2/flk3 ligand. (Nicola, et al., Blood 54:614-627, 1979; Golde et al., Proc. Natl. Acad. Sci. (USA) 77, 593-596, 1980; Lusis, Blood 57, 13-21, 1981; Abboud et al., Blood 58, 1148-1154, 1981; Okabe, J. Cell. Phys., 110, 43-49, 1982; Fauser et al., Stem Cells, 1, 73-80, 1981). Preferably, the culture will include at least c-kit ligand and IL-3. More preferably, the culture will include c-kit ligand, IL-3, IL-6 and GM-CSF. In one embodiment, the cytokines are contained in the media and replenished by media perfusion. Alternatively, when using a bioreactor system, the cytokines may be added separately, without media perfusion, as a concentrated solution through separate inlet ports. When cytokines are added without perfusion, they will typically be added as a 10× to 100× solution in an amount equal to one-tenth to 1/100 of the volume in the bioreactors with fresh cytokines being added approximately every 2 to 4 days. Further, fresh concentrated cytokines also can be added separately in addition, to cytokines in the perfused media.

The population is then cultured under suitable conditions such that the cells condition the medium. Improved expansion of purified stem cells may be achieved when the culture medium is not changed, e.g., perfusion does not start until after the first several days of culture.

In most aspects, suitable conditions comprise culturing at 33 to 39, and preferably around 37° C. (the initial oxygen concentration is preferably 4-8%, and most preferably, about 5%) for at least 6 days and preferably from about 7 to about 10 days, to allow release of autocrine factors from the cells without release of sufficient waste products to substantially inhibit stem cell expansion. After that time, the oxygen concentration is preferably increased to about 20%, either stepwise or gradually over the remainder of the culture period, which will typically be for a total of 10-28 days. Preferably, bone marrow stem cells will be grown for around 21 days and mobilized peripheral blood stem cells will be cultured for around 14 days.

After the initial culture period without medium exchange, the culture medium is exchanged at a rate which allows expansion of the stem cells. In a system where no variable volume is used, medium is exchanged on day 7 (for mobilized peripheral blood stem cells) or on day 10 (for bone marrow cells). The exchange of fresh medium in a perfused system is preferably laminar. This uniform, nonturbulent, flow prevents the formation of "dead spaces" where patches of cells are not exposed to medium. The medium is exchanged at a rate of from about 0.10/day to 0.50/day or 1/10 to 1/2 volume exchange per day. Preferably, the perfusion rate will be from about 0.25/day to 0.40/day. Most preferably, for bone marrow stem cells, perfusion will be at a rate of 0.27/day starting around day 14, and for mobilized peripheral blood stem cells, perfusion starts at 0.25/day around day 10 and increases to 0.40/day around day 12.

Preferably, the cell concentration is kept at an optimum throughout expansion. For instance, stem cells can expand up to ~1500 fold compared to a mononuclear cell (MNC) population which expands only ~10-20 fold. Stem cells have a large proliferative capacity, as such, where culture is performed in a closed system such a system must provide enough volume for total cell expansion. However, stem cells also require a relatively high inoculation density. Optimal inoculation density and proliferation conditions can be achieved by growing the cells in a bioreactor such as the one described in U.S. Pat. No. 5,728,581. The cells are seeded at the appropriate cell density in a depression and additional media are added when an appropriate cell density is attained. The shape of the device allows the medium volume to be increased up to threefold without significantly reducing the oxygen transfer efficiency to the cells.

Use of Reprogrammed Cells

Ex vivo expanded hematopoietic stem cells have been used in various clinical trials and many practitioners predict that hematopoietic stem cells may be useful in treating or ameliorating numerous diseases. Despite this exciting potential, the mechanisms controlling gene expression in these cells and, indeed, the mechanisms by which hematopoietic cells differentiate, are not yet understood. The methods of the present invention show how to expand HSC populations in culture in manner in which the HSC retain their capacity to self-renew and differentiate.

A particular use for the genes of the present invention will be in autologous bone marrow transplants for individuals suffering from bone marrow aplasia or myelosuppresion such as that seen in response to radiation therapy or chemotherapy. High dose or lethal conditioning regimens using chemotherapy and/or radiation therapy followed by rescue with allogeneic stem cell transplantation (allo-SCT) or autologous stem cell transplantation (ASCT) have been the treatments of choice for patients with a variety of hematologic malignancies and chemosensitive solid tumors resistant to conventional doses of chemotherapy. A common source of stem cells for such procedures has been the bone marrow. Recently, peripheral blood stem cells (PBSC) have also been used. It is contemplated that the methods of the present invention will yield HSC populations that may be used for such stem cell transplantation.

Autologous bone marrow transplant (ABMT) is an example of ex vivo therapy which employs HSC populations isolated from the patient, treated with a therapeutic modality and reintroduced into the patient. In ex vivo therapy, cells from the patient are removed and maintained outside the body for a period of time. During this period, the cells are expanded according to the methods of the present invention and then reintroduced into the patient. In ABMT, the patient will serve as his/her own bone marrow donor. Thus, in preferred embodiments, the methods of the present invention are used in conjunction with cancer therapy in which a normally lethal dose of irradiation or chemotherapy may be delivered to the patient to kill tumor cells, and the bone marrow repopulated with the patients own cells that have been maintained and expanded ex vivo. Reintroducing into the patient a HSC population that has been grown according to the methods of the present invention will be particularly useful in patients that are undergoing chemotherapy or radiation that destroys the bone marrow of the patient.

In particular embodiments, the methods of the present invention are used in ABMT for gene therapy, wherein the HSC are transformed with a gene of interest that is to be introduced into the patient. In such embodiments, a therapeutic gene is introduced into the cells prior to expansion of the cells, after which the cells are expanded and are reintroduced into the patient. Any gene therapy that is amenable to introduction to the host cell through the using HSC may eb accomplished using the HSC cells of the present invention. For example, gene therapies have been contemplates that reintroduce into an subject genes such as α-globin, β-globin, γ-globin, a cytokine, β-interferon, g-interferon, cytosine deaminase, adenosine deaminase, b-glucoronidase, p53, p16, p21, MMAC, p73, BRAC1 (see e.g., WO 98/56938, incorporated by reference as providing a teaching of the types of genes that may be used for gene therapy). Polypeptide growth factors and hormones, such as epidermal growth factor (EGF), insulin, insulin-like growth factor-I (IGF-I), platelet derived growth factors (PDGF-A and -B and other members of the PDGF family) and fibroblast growth factors (FGFs)

(Heldin et al., Cell Regulation, 1: 555-566 (1990); Ullrich et al., Cell, 61: 243-54 (1990)) are thought to be excellent candidates for gene therapy.

Gene therapy approaches involving the present cells involve, in one embodiment, preparation of the HSC according to the methods described herein, exposure of the isolated cells to a gene delivery vector and re-infusion of the modified cells into the patient (Smith, J. Hematother. 1:155 (1992)). Gene therapy can be useful in treating, for example, congenital diseases, such as sickle cell anemia, in which case the mutant β-globin gene is replaced or supplemented with either the wild type globin gene or an anti-sickling globin gene. In the treatment of cancer, drug resistance genes can be introduced into the HSC population cells to confer resistance to cytotoxic drugs. This can reduce the incidence and severity of myelosuppression. For the treatment of infectious diseases, including HIV, anti-viral genes can be introduced into the cells so that they are rendered resistant to the virus (Gilboa and Smith, *Trends in Genetics* 10:139 (1994)). Methods and compositions for accomplishing gene transfer into cells are described in U.S. Pat. No. 5,942,496. Such methods may be useful in the accomplishing gene transfer into the cells of the present invention.

Thus, the present invention contemplates a method of treating a human patient having a pathogenic cell disease which requires administration of stem cells expanded according to the methods described herein. Preferably, the stem cells are peripheral blood stem cells, cord blood stem cells or bone marrow stem cells. The HSCs expanded according to the methods provided herein may be used in the treatment of any clinical diseases involving hematopoietic dysfunction or failure, either alone or in combination with other lymphokines or chemotherapy. Such disorders include leukemia and white cell disorders in general. The HSCs can be used in induced forms of bone marrow aplasia or myelosuppression, in radiation therapy or chemotherapy-induced bone marrow depletion, wound healing, burn patients, and in bacterial inflammation, among other indications known in the art.

Pathogenic cell diseases treatable with the methods include malignant diseases such as chronic myelogenous leukemia, acute myelogenous leukemia, acute lymphoblastic leukemia, non-Hodgkin's lymphoma, myelodysplastic syndrome or multiple myeloma. The malignant disease may also be a solid tumor as in metastatic breast cancer. The disease being treated alternatively may be a non-malignant diseases such as β-thalassemia major, Blackfan Diamond Anemia, Gaucher's anemia, Fanconi's anemia or AIDS. The non-malignant disease may also be an autoimmune disease.

EXAMPLES

The following examples are included to demonstrate preferred embodiments of the invention. It should be appreciated by those of skill in the art that the techniques disclosed in the example which follows represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention

Example 1

Materials and Methods

The present example provides some exemplary materials and methods that may be used in conjunction with the present invention to determine expansion of a given population of HSC cells. Certain of these methods were used to obtain the data presented herein below. However, it should be understood that these methods may be adapted and still produce data useful in interpreting the present invention.

Isolation of Human CD34+ Cells

Those of skill in the art are aware of numerous techniques by which to isolate cells that have particular markers that identify the cell as being of a certain lineage. HSC cells are often isolated initially as being that population of cells that have a $CD34^+$ phenotype. The following description provides one exemplary methods for such an isolation that was used by the inventors.

Cryopreserved cadaver adult human bone marrow (BM) mononuclear cells (MNC) were rapidly thawed at 37° C. and slowly diluted dropwise in RMPI (Biowhittaker, Walkersville, Md.) containing 10% heat inactivated fetal bovine serum (FBS) (HyClone laboratories, Logan, Utah) and 0.1 mg/mL Dnase I (Boehringer Mannheim, Indianapolis, Ind.) before further purification, and left to stand for 45 minutes at room temperature. $CD34^+$ cells were immunomagnetically enriched using magnetic activated cell sorting (MACS) CD34+ Isolation Kit (Miltenyi Biotec, Auburn, Calif.) according to the manufacturer's instructions. Briefly the MNC's were washed and resuspended in $Ca^{2+}$-free and $Mg^{2+}$-free Dulbecco modified phosphate-buffered saline (DPBS) (Biowhittiker, Walkersville, Md.) supplemented with 0.5% bovine serum albumin (BSA) (Sigma Chemical Co., St. Louis, Mo.) and 2 mmol/L ethylenediamine tetraacetic acid (EDTA). Cells were incubated with hapten-labeled anti-$CD34^+$ monoclonal antibody (moAb) (QBEND-10) in the presence of Fc blocking reagent, and then with anti-hapten coupled to microbeads. Labeled cells were filtered through a 30 μm nylon mesh and separated using a high gradient magnetic separation column. Magnetically retained cells were then flushed out and used for the experiments. These cells were eluted and stained using moAb against a different epiptope of CD34 (HPCA 2) to determine the purity of $CD34^+$ cells enriched BM and analyzed for phenotype and purity using flow cytometric methods (see below). The purity of the CD34+ populations routinely ranged from 90%±2.3%.

Ex-Vivo Expansion Cultures

As indicated herein throughout, it will be useful to expand HSC populations ex vivo. The following description details an exemplary expansion of $CD34^+$ cells, used by the inventors herein, that one of skill in the art could readily modify.

To promote cell division of isolated $CD34^+$ cells, a stroma-free suspension culture was established as previously described (Bazil et al., 1995). Tissue culture dishes (35 mm; Costar, Corning, N.Y.) were seeded with $1 \times 10^5$ $CD34^+$cells/well in 2.5 mL Iscove modified Dulbecco medium (IMDM) (Biowhittaker, Walkersville, Md.) containing 30% FBS and a cocktail of cytokines specifically thought to promote exit from $G_0/G_1$ in primitive HSC populations which consisted of 100 ng/mL recombinant stem cell factor (SCF), 100 ng/mL FLT-3 ligand, 100 ng/mL thrombopoetin (TPO) and 50 ng/mL of interleukin (IL)-3, (all from Amgen Inc., Thousand Oaks, Calif.).

Cells were maintained in the media and incubated at 37° C. in a 100%-humidified atmosphere containing 5% $CO_2$ for 48 hours. After intial 16 hours of incubation cells were exposed to the demethylating agent, 5-aza2'deoxycitidine (5azaD) (Sigma Chemicals, St. Louis, Mo.) at a concentration of $10^{-6}$M. After 48 hours, cells were washed by centrifugation and then equally distributed to new tissue culture dishes in 2.5 mL IMDM supplemented with 30% FBS containing cytokines known to promote terminal differentiation of HSC into multiple hematopoietic lineages. The cocktail of cytokines contained 100 ng/mL of SCF, 50 ng/ml of granulocyte colony-stimulating factor (G-CSF), 50 ng/mL of IL-3, 50 ng/ml of IL-6 and 5 units (U)/mL of recombinant erythropoietin (EPO) (Amgen Inc., Thousand Oaks, Calif.). Cells at this time point were exposed to Trichostatin (TSA) (Sigma Chemical., St. Louis, Mo.) at 5 ng/mL and the culture was continued for an additional 7 days. At the end of the culture period cells were counted for viability by the trypan blue exclusion method using an inverted microscope. 5-fluorouracil (5-FU) (Sigma Chemical., St. Louis, Mo.) was used at a concentration of 200 μg/ml and added at the 16 hour time point instead of 5azaD and the cultures carried on as described above with no addition of TSA.

COBRA Assay Method and Bisulfite Sequence Analysis

The following section provides an exemplary description of the COBRA assay and bisulfite sequence analysis to quantitate DNA methylation.

DNA was prepared from cultured $CD34^+$ cells (0.5-2.0× $10^6$ total cells) using the QIAamp DNA blood Minikit (Qiagen, Valencia, Calif.) according to manufacturer's instructions. The purified DNA was digested with 10-20 units Hind III at 37° C. for one hour followed by two extractions with a 50/50/1 mixture of phenol/chloroform/isoamyl:alcohol saturated with 0.5 M Tris, pH 7.5. The digested DNA was precipitated overnight at −20° C. in the presence of 2.5 volumes ethanol and 0.3 M sodium acetate, pH 7.0. DNA was harvested by centrifugation, washed 2× in 70% ethanol and dissolved in $H_2O$.

DNA Denaturation was performed by incubation of 1-2 μg DNA in 10-20 μl 0.3 M NaOH at 37° C. for 20 minutes. Bisulfite modification was performed by the addition of 200 μl bisulfite solution (2.5 M sodium metabisulfite, 100 mM hydroquinone) prepared according to the method as described (Clark et al., Nucleic Acid Res. 22:2990-2997, 1994; Raizis et al., Anal. Biocem; 226:161-166, 1995; Xiong et al., Nucleic Acid Res., 2532-2534, 1997), followed by incubation for 4 hours at 50° C. The bisulfite-modified DNA was purified using the Wizard DNA Clean up System (Promega, Madison, Wis.) according to the manufacturer's instructions. Desulphonation of the busulfite-modified DNA was performed by the addition of 1/10 volume of 3M sodium acetate, pH 7.0, and 1/10 volume 3 M NaOH followed by incubation at 37° C. for 20 minutes. The desulphonated DNA was precipitated in the presence of 2.5 volumes ethanol at −20° C. overnight.

For COBRA (Combined Bisulfite Restriction Analysis), a 201 bp fragment of the γ-globin promoter region was amplified by two rounds of PCR using doubly nested primers. Primers for the first round of amplification were AAAAGAAGTTTTGGTATTTTTTATGATGGG (30mer; sense) and TCCTCCAACATCTTCCACATTCACCTTAC (29mer; antisense) for the second round were TGGGAGAAGAAAATTAGTTAAAGGG (25mer; sense) and AATCAAAACAAAACTAACCAACCC (24mer; antisense). PCR was performed using hot start conditions according to the following scheme (2 cycles at 94° C., 2 min-50° C., 3 min-72° C., 2 min; 33 cycles at 94° C., 2 min-50° C., 2 min-72° C., 2 min; 1 cycle at 94° C., 2 min-50° C., 2 min-72° C., 7 min). 5-10 μl PCR product was digested with 10-20 units Hinfl at 37° C. for 2 hours. The PCR product is cleaved by Hinfl into two fragments of 56 and 145 bp only if the CpG residue at −256 is methylated in the original DNA sample. Digested products were analyzed by polyacrylamide gel electrophoresis (5% gel), visualized by staining with ethidium bromide, and quantified by densitometry.

Methylation of the ε- and γ-globin promoters was measured by bisulphite sequence analysis. Following bisulfite modification, a γ-globin promoter fragment containing five CpG residues at −54, −51, +5, +16, and +48 was amplified using nested PCR. An additional fragment containing 3 CpG residues was also amplified from the ε-globin promoter. PCR products were cloned in the pCR4 vector (TOPO TA cloning kits, Invitrogen, Carlsbad, Calif.). Mini-prepped DNA from individual random clones was sequenced using an ABI Prism 300 Genetic Analyzer by the DNA Sequencing Facility of the University of Illinois at Chicago Research Resources Center.

Monitoring Cell Division

Carboxyfluorescein diacetate succinimidyl ester (CFSE) labeling was used to assess cell division. Freshly isolated $CD34^+$ cells were labeled for 10 min at 37° C. with 0.5 μmol of CFSE (Lamda, Graz, Austria) PBS, a cytoplasmic dye that is equally diluted between daughter cells, and washed three times with 10% FBS RMPI 1640. CFSE labeled cells were then cultured as mentioned above for 9 days and were analyzed for fluorescence intensity, using a FACS Caliber cytometer on day 5 and day 9 (Lyons et al., J. Immunol. Methods 171:131-7, 1994).

FACS

The phenotypic characteristics of the $CD34^+$ cells were analyzed using FACS. After 9 days of culture, expanded marrow $CD34^+$ cells were analyzed for primitive HSC phenotype, previously defined, by using flow activated-cell sorter (FACS) (Becton Dickinson (BD) FACS Calibur, San Jose, Calif.). Cells were stained with anti-human $CD34^+$ moAb conjugated either to fluorescein isothiocyanate (FITC) or phycoerythrin (PE) and another moAb including anti-CD38, anti-CD117, anti-CD90. To determine the lineage positive cells a panel of moab all conjugated to FITC (anti-CD2, anti-CD14, anti-CD15, anti-CD19 and anti-GlyA) (all antibodies were purchased from BD) were utilized. All anaylsis were paired with the corresponding matched isotype control of the specific moAb utilized. All staining and washes were performed in DPBS (Biowhittaker, Walkersville Md.) and 0.5% BSA (Sigma, Chemicals Co., St. Louis, Mo.). Immediately prior to FACS anaylsis, 2 g/mL propidium iodide (PI) (Sigma, Chemicals Co., St. Louis, Mo.) was added for the exclusion of nonviable cells for phenotypic analysis. Using Cell-Quest software (BD), at least 10,000 live cells were acquired for each analysis.

Colony-Forming Cell Assays

Colony-forming cells (CFC) were assayed under standard conditions in semisolid media as previously described (Brandt et al., Blood 94:106-113, 1999). Briefly $1 \times 10^3$ primary $CD34^+$ cells or unfractionated cultured cells exposed to different conditions used following 9 days of culture were plated in duplicate cultures containing 1 ml IMDM with 1.1% methylcellulose, 30% FBS, $5 \times 10^{-5}$ M 2-mercaptoethanol (Methocult, Stem Cell Technologies, Vancouver, BC, Canada), and a cocktail of growth factors including 100 ng/ml of SCF, 5 U/mL of EPO, 50 ng/mL of IL-3, 50 ng/mL of IL-6 and 50 ng/mL of G-CSF (Amgen Inc., Thousand Oaks, Calif.). The cells were plated into 35 mm tissue-culture dishes (Costar), and after 14 days of incubation at 37° C. in a 100%-humidified atmosphere containing 5% $CO_2$, the colonies were scored with an inverted microscope following standard criteria (Breems et al., Leukemia, 8:1095-1104, 1994).

After 7 weeks of passage in vivo of human grafts in NOD/SCID mice, marrow cells from mice were then plated in methylcellulose assays at 100,000 cells/plate as previously described. After 14 days of incubation the number of hematopoietic colonies were enumerated.

Cobblestone Area-Forming Cell Assays

The ability of primitive HSC to form cobblestone areas (CA) in long term marrow cultures has been used as an in vitro surrogate progenitor HSC assay (Breems et al., *Leukemia,* 8:1095-1104, 1994, Lefkovits et al., *Immunol. Today,* 5:265-268, 1984; Cross et al., *Curr. Opin. Genet. Dev.,* 5:609-613, 1997). CD34$^+$ cells after 9 days of culture from each condition were plated in limiting dilution in flat-bottomed 96-well plates (Costar) onto confluent, irradiated (7000cGy) monolayers of the murine stromal fibroblast line M2-10B4 (a gift from Dr. C. Eaves, Vancouver, BC, Canada). Each well contained 200 μL of a 50:50 mixture of IMDM and RPMI with 10% FBS. A cocktail of growth factors, including 100 ng/mL SCF, 100 ng/mL leukemia inhibitory factor (LIF), 50 ng/mL IL-3, 50 ng/mL IL-6 and 50 ng/mL granulocyte-monocyte colony stimulating factor (GM-CSF) (Amgen, Thousand Oaks, Calif.).

The cultures were fed weekly by replacement of one half of the culture volume with fresh medium containing the above cytokines at 2 times the previously defined concentration. After 5 weeks of culture in a humidified incubator at 37° C. containing 5% $CO_2$, the number of CA were ennumerated. The CAFC frequency was computed by means of minimization of chi regression to the cell number at which 37% of wells were negative for CA formation, with 95% statistical precision using L-Calc (Limiting dilution calculation) software (Stem Cell Inc., Vancouver, Canada; Lefkovits et al., *Curr. Opin. Genet. Dev.* 5:609-613, 1997).

Assay for Marrow-Repopulation

The present invention describes methods of HSC expansions in which the cells maintain the self-renewal capacity of HSC. One method of demonstrating that the cells retain such capacity is to test the cells in vivo to determine whether the expanded HSC population retain such capacity in vivo. Such in vivo assays may be performed in mouse models. One such model is the well-known NOD/SCID model.

A colony of immunodeficient nonobese diabetic/ltsz-scid/scid (NOD/SCID) mice were purchased from the Jackson Laboratories (Bar Harbor, Me.) and were maintained as previously described (Coneallt et al., Proc. Nat'l Acad. Sci. USA, 94:9836-41, 1997). All NOD/SCID mice were kept under sterile conditions in the microisolator cages and were provided with autoclaved food and acidified water.

Mice were given 300cGy of total body gamma irradiation and human grafts were injected via the tail vein. Cytokines including SCF, IL-3 and GM-CSF at 5 ug/mouse were injected intraperitoneally on alternate days following injection of human grafts during the first week of transplant. Sulfamethoxazole (40 mg/mL) and Trimethoprim (8 mg/mL) (SMX/TMZ; Elkins-Sinn, Cherry Hill, N.J.) were added in the drinking water for 3 days post injection and then subsequently for 3 days beginning the second week of transplant. Mice were sacrificed after 7 weeks. Femurs and tibias were flushed with Hank's balanced salt solution (HBSS) (Biowhittiker) with 2% FBS (Hyclone) and 0.02% sodium azide and cell counts performed. Cells were preincubated with 1 mg/ml of human gamma globulin in staining to block human Fc receptors. Murine Fc receptors were blocked by a second incubation of the cells in 2.4G2 (an anti-mouse Fc receptor moAb). Marrow cells were analyzed by flow cytometry to detect human cell engraftment as previously described.[29] Briefly to quantitate the total number of human cells present an aliquot of cells was stained with anti-CD45-FITC(BD) and anti-CD71-FITC(BD). This aliquot was also stained with anti-CD19-PE(BD) and cyanine-5-succinimidyl-labeled anti-CD34 (BD). After 7 weeks, marrow cells were plated in methylcellulose as previously described. Colonies from these CFC were then pooled and stained with moAb against CD33 and CD45 (BD) to assess the presence of human cells.

Example 2

Initial Studies Showing Role of HSC Methylation and Acetylation in Reprogramming HSC Behavior In Vitro Epigenetically mediated loss of gene function has been shown to be accompanied by DNA methylation of a gene's promoter and by histone deacetylation. Thus, conditions previously utilized for in vitro stem cell expansion result in silencing of genes required for hematopoetic stem cells (HSC) to undergo symmetrical cell division.

In order to study this phenomenon further, adult human bone marrow CD34+ cells were cultured in media containing IL3, TPO, SCF and FLT-3 for 48 hours in order to promote cell division. The cells also were exposed to conditions and different time points. The cells were exposed to an inhibitor of DNA methylation (IDM), 5 aza 2'dexoxycitidine (5azaD) or the cytotoxic agent 5-flurouracil (5-FU). The cells were then exposed to conditions (SCF, IL-3, IL-6, GM-CSF and EPO) known to promote cell differentiation. Trichostatin A(TSA), a histone deaceytlase inhibitor (HDACI), was added at different time points after the exposure to 5azaD to further prevent possible gene silencing.

The cultures were allowed to expand for 9 days and the test performed on day and the data retrieved from those tests is depicted in FIG. 2-4 and tables 1 through 6. The tests performed included DNA methylation, cell phenotype, CFC potential, CAFC potential and engraftment.

DNA methylation status was analyzed using COBRA (Combined Bisulfite Restriction Analysis; see e.g., Xiong et al., *Nucleic Acids Res.* 15; 25(12):2532-4, 1997) to quantitate the DNA methylation status of a CpG residue located at −256 position within the γ-globin promoter region. Only 10% of the primary CD34+ cells, and 14% of the cells cultured for five days in the absence 5azaD and TSA, were hypomethylated; by contrast 40-70% of the cells treated with 5azaD and TSA (drug treated) at various concentrations and combinations were hypomethylated. After 9 days the control cultures contained 2% CD34+ cells that were all CD90− (Thy-1) and CD133−. By contrast 64% of the cells treated with 5azaD and TSA in combination were CD34+, of which 50% were CD90+ and 28% CD133+. After 9 days there was a 2-4 fold increase in the absolute number of CD34+CD90+ cells in drug treated cultures (22000-100,000). By contrast the CD34+ cells after being exposed to 5-FU alone contained 20% CD34+ cells of which only 10% were CD90+ at day 9 resulting in decline in absolute numbers of CD34+CD90+ cell (22,000-700) in the culture.

In order to enhance the synergy between the actions of 5azaD and TSA, TSA was added 80 hours after the initial exposure of the cells to 5azaD, a strategy which resulted in a 7 fold increase in CD34+CD90+ cells (22,000-160,000). Of the total number of cells in the day 9 drug treated cultures, 60% were CD34+ of which 73% were CD90+. After 9 days the control cultures contained assayable CFU-GM but no erythroid or multipotent progenitors, while 50% of the progenitor cells assayed from the drug treated cultures produced multilineage colonies containing erythroid cells. Surprisingly, the percentage of multilineage progenitors in the 5azaD and TSA treated cultures at day 9 were 5 fold greater than the primary cells.

Cells from the 5-FU treated cultures after 5 days contained no assayable hematopoietic progenitor cells. The cloning efficiency of the primary selected CD34+ was 14.2%, whereas that of the unfractionated control cells at day 9 of culture was 1.1% while the cloning efficiency of unfractionated cells within the drug treated cultures was 11.0%. These studies suggest that the behavior of human CD34+ cells in vitro can be altered by the sequential addition of IDM and a HDACI but not the cytotoxic agent 5-FU. Such pharmacologic agents not only result in the expansion of the numbers of cells expressing a primitive phenotype but also alters the differentiation program that leads to a persistent capacity to generate multipotent progenitors. Alteration of HSC methylation and acetylation appear to present a useful alternative approach towards reprogramming HSC behavior in vitro.

Example 3

Methylation Status of Marrow $CD34^+$ Cells with and without 5azaD and TSA

To determine the methylation status of treated and untreated $CD34^+$ marrow cells COBRA (Combined Bisulfite Restriction Analysis) was used to quantitate the DNA methylation of a CpG residue located at $-256^{th}$ position within the γ-globin promoter region. Primary $CD34^+$ cells (day 0) initially were methylated at this promoter site (90%). These cells were then cultured for 5 days under various conditions outlined (Table 7). 87% of cells cultured for five days with cytokines alone were methylated suggesting that the status of this promoter was unchanged throughout the culture period. By contrast 58% of the cells treated with cytokines and sequential addition of 5aza2'deoxycitidine (5azaD) and Trichostatin (TSA) were methylated after culture (Table 7) indicating that these drugs might be capable of altering their methylation pattern in vitro.

Bisulfite sequence analysis of 5 CpG sites within the γ-globin gene promoter and 3 CpG sites within the ε-globin promoter was performed to confirm and extend the results of the COBRA assay. Six clones were sequenced from both the cells exposed to cytokines alone and from the cells exposed to cytokines and sequential 5azaD and TSA. Clones from the cells exposed to cytokines alone were completely methylated (100%) at all sites in all clones. In the cells exposed to sequential 5azaD and TSA 21/30 CpG sites within the γ-globin promoter were methylated (70%), and 12/18 sites were methylated within the ε-globin promoter (67%) (Table 7). It is important to point out that hypomethylation of the γ-globin gene promoter has little influence on stem cell behavior. These studies were however performed to show that 5azaD was capable of achieving hypomethylation of a particular gene.

Example 4

Cell Division $CD34^+CD90^+$ Cells in Culture

Figures 5A, 5B, 5C:
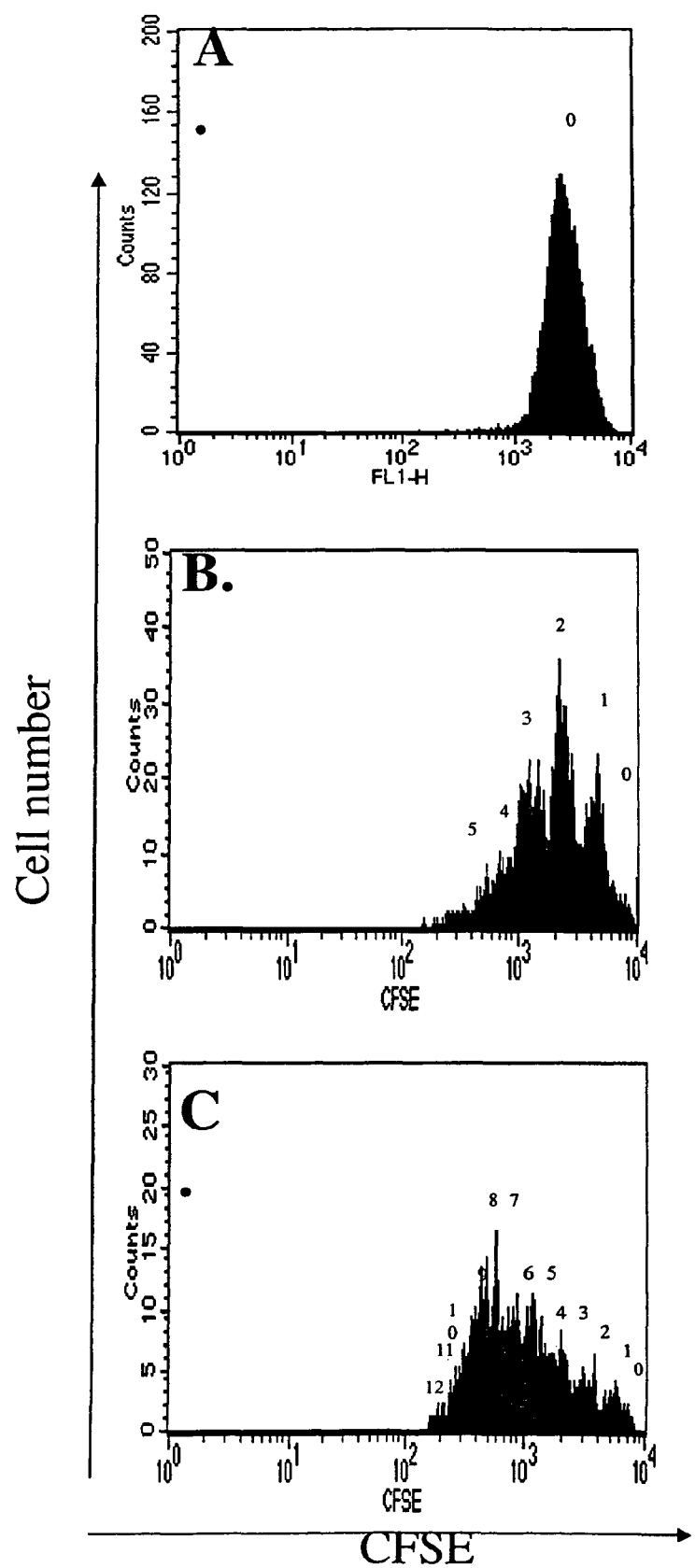

Cell division of $CD34^+/CD90^+$ cells was determined in vitro. Cells were analyzed after 5 and 9 days of incubation for their division history utilizing CFSE staining technique. As shown in FIG. 5, by gating on the $CD34^+CD90^+$ cell population these cells underwent multiple cell divisions at both time points. These studies demonstrate that the phenotype and functional effects attributed to 5azaD and TSA are not due to preservation of quiescent cells but rather occur subsequent to multiple cell divisions.

Example 5

Phenotype of $CD34^+$ Following Drug Treatment

The phenotype of the cells prior to and after treatment with cytokines in vitro for a period of 9 days (Table 8). $CD34^+$ marrow cells were immunomagentically selected as described in Example 1. A 2-step culture system was set up to determine the phenotype of the selected cells. The cells were initially cultured in cytokines that promote HSC division to ensure cycling and thus allow for the incorporation of 5azaD which was added after 16 hours of this culture. At 48 hours TSA was added and the cytokines were changed to those that promote differentiation. This was done to drive the cells towards differentiation and to try and detect a change in phenotype and function in the presence of an extreme external milieu favoring differentiation rather than proliferation and self renewal.

After culture in cytokines alone, a progressive decline in the percentage and absolute number of $CD34^+$ cells was observed, a decline also was seen in the percentage of $CD34^+$ cells expressing a HSC phenotype ($CD90^+$, $CD38^-$, c-kit$^{lo}$, lin$^-$). In particular there was a significant decrease in the absolute number of $CD34^+CD90^+$ cells in these cultures (Table 9). By contrast the $CD34^+$ cells exposed to the same cytokines and sequential 5azaD and TSA retained the primitive HSC phenotype (Table 8) resulting in an expansion of $CD34^+CD90^+$ cell numbers (Table 9). Cells exposed to cytokines and to either 5azaD or TSA alone had a more limited expansion of $CD34^+CD90^+$ cells (Table 9).

To show that this effect could not be attributed merely to cytotoxicity, 5-FU was added to cultures instead of the 5azaD. In vitro 5-FU treatment has previously been utilized to select for primitive human progenitor cells in vitro (Berardi et al., Science, 267:104-108, 1995). The $CD34^+CD90^+$ cell number initiated with 5-FU treated $CD34^+$ cells decreased significantly after 9 days of culture (Table 9) so that by day 9 no $CD34^+CD90^+$ cells were observed.

Example 5

Functional Analysis of Expanded Marrow $CD34^+$ Cells Exposed to 5azaD and TSA

To ensure that a discordance between the phenotype and function of the drug treated progenitor cells did not exist, the functional potential of these cells was evaluated by 2 different in vitro assays including the colony forming cell assay (CFC) and cobblestone area forming cell (CAFC) assay. These assays are are used to quantitate the number of differentiated and primitive HPC, respectively. In addition, the ability of these various cell populations to engraft in vivo and differentiate into multiple hematopoietic lineages in immunodeficient NOD/SCID mice (SCID repopulating assays) was used as a surrogate assay for marrow repopulating potential, a unique characteristic of primitive HSC.

Cells treated with cytokines alone for 9 days contained dramatically reduced numbers of assayable progenitors in comparison to primary cells (Table 10). By contrast, cells from cultures treated with cytokines and sequential 5azaD and TSA contained similar numbers of progenitor cells as that assayed from primary cells. Significantly, the drug treated cultures contained greater numbers of multilineage progenitor cells than the primary cells (Table 10). By contrast, cells assayed from the cultures treated with cytokines and 5-FU contained no assayable hematopoietic progenitor cells. The plating efficiency of $CD34^+$ cells plated immediately after selection (primary CD34+ cells) was 12.2%±0.5%, whereas that of the unfractionated control cells after 9 days of culture in cytokines alone was 0.8%±0.2. The plating efficiency of the unfractionated cells exposed to cytokines in combination with 5azaD and TSA was 9.7%±0.2% which was comparable to the primary CD34+ selected cell population.

Figure 6:
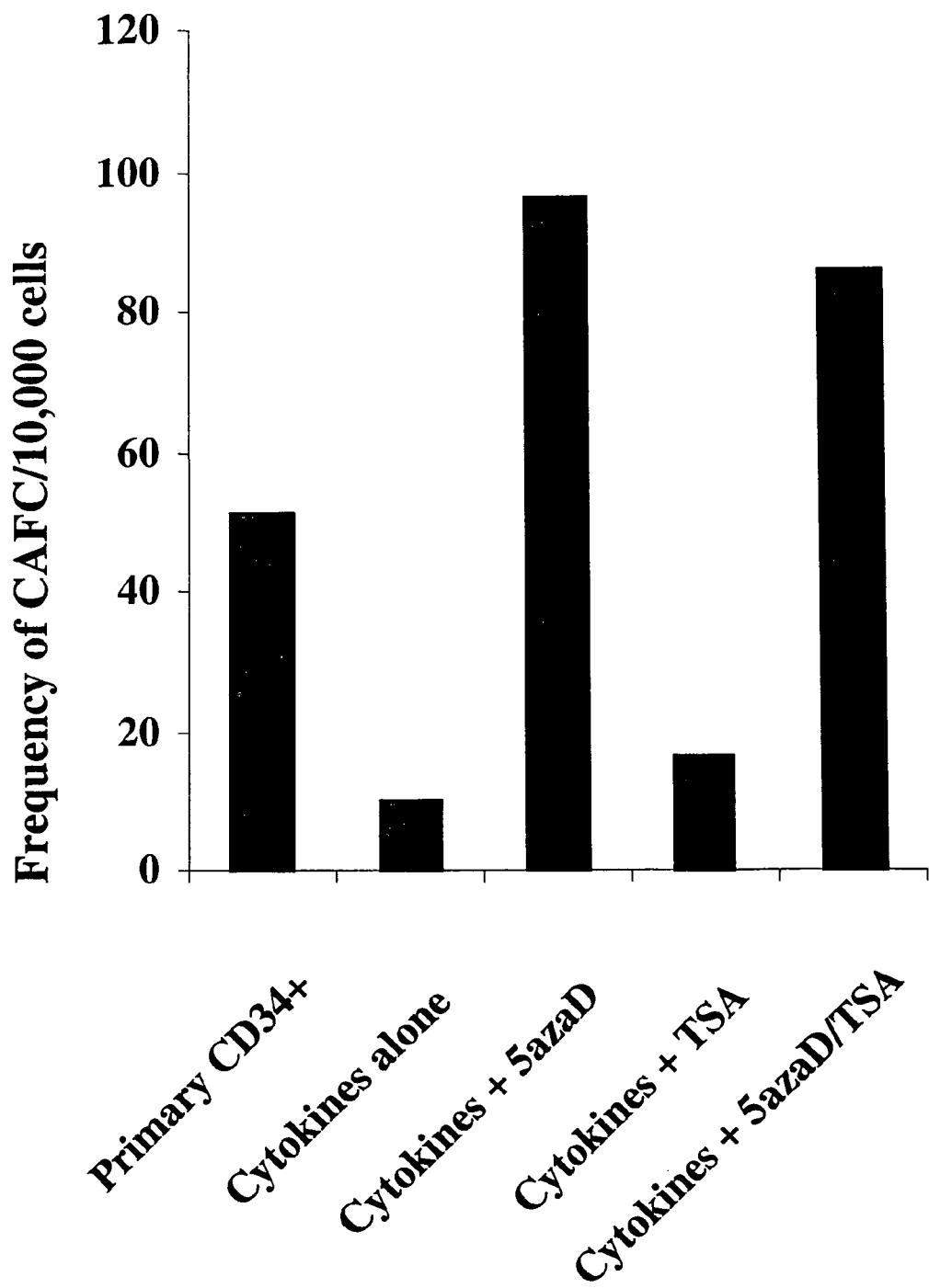
FIG. 6. Frequency of CAFC after 9 days of culture in different conditions. Cells were plated in a limiting dilution in CAFC surrogate assay on a stromal layer in different conditions as shown in the figure. The number of CA was expressed out of 10,000 cells plated. CAFC frequency was computed using minimization by regression to the cell number at which 37% of wells showed negative CAFC growth with 95% statistical precision.

To determine if the drug treated (sequential 5azaD and TSA) CD34+ cells also contained more primitive HPC, cultured cells were assayed for their ability to form cobblestone area (CA) in long term marrow cultures (FIG. 6). The CA forming cells (CAFC) is a well established surrogate assay for primitive HPC Which resemble HSC. The primary CD34+ cells had a frequency of 50, CAFC/10,000 CD34+ cells plated, while the cells exposed to cytokines alone demonstrated a 5 fold reduction in that frequency (10 CAFC/10,000 cells). By contrast, the CD34+ cells exposed to cytokines and sequential 5azaD and TSA enjoyed a 1.7 fold increase in the number of CAFC (86 CAFC/10,000 cells) over that of the primary cells. Cells exposed to 5azaD alone were characterized by a 1.9 fold (96 CAFC/10,000 cells) increase in the CAFC indicating that demethylation might play a critical role in reactivating genes at the level of the CAFC. By contrast cultures treated With TSA alone contained comparable numbers of CAFC as cultures receiving cytokines alone (FIG. 5).

Figure 7:
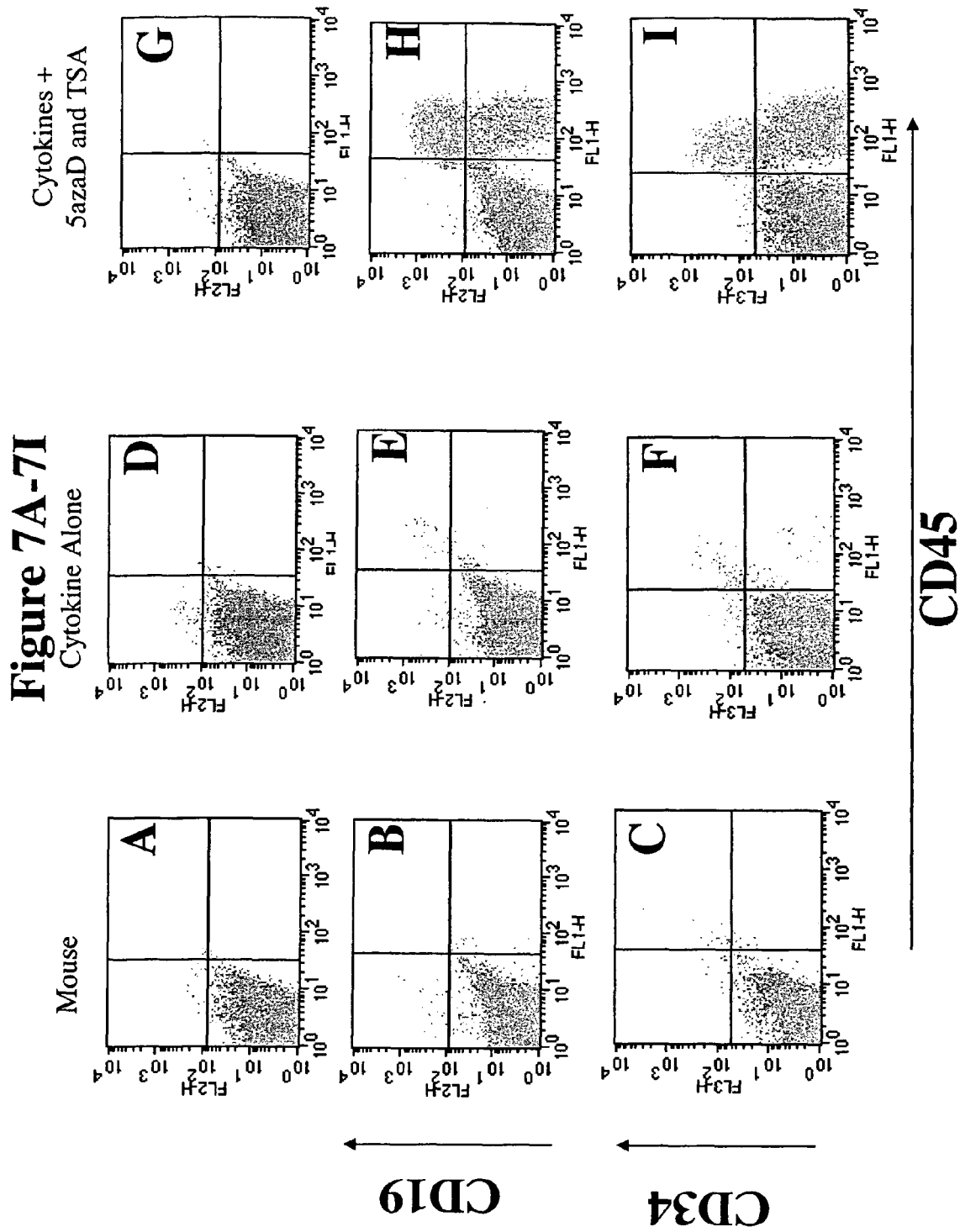
FIG. 7. FACS anaylsis of marrow cells isolated from NOD/SCID mice 7 weeks after injection of human cell grafts. Cells were stained for human CD45, CD19, CD41, CD34 to assess multilineage engraftment.
Figure 8:
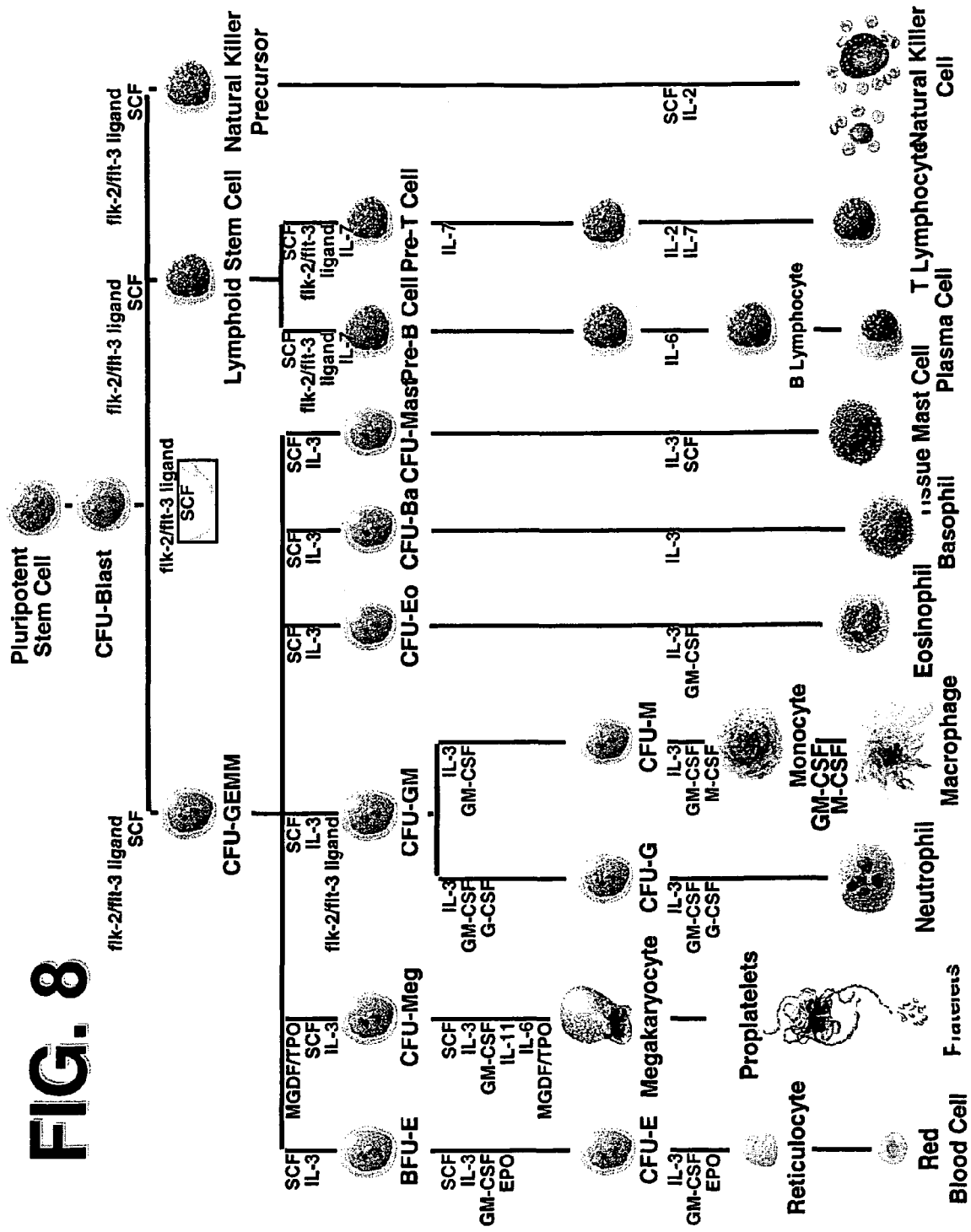
FIG. 8. Schematic of Hematopoiesis.

The ability of human HSC to engraft and differentiate into multiple hematopoietic lineages in vivo is an established surrogate functional HSC assay (Coneally et al., *Proc. Nat'l Acad. Sci. USA*, 94:9836-41, 1997). Primary CD34+ cells engrafted NOD/SCID mice and were capable of generating human CD34+ and CD19+ cells in vivo while cells exposed to cytokines alone (FIG. 7) or cytokines and TSA no longer possessed such marrow repopulating activity. However, both cells exposed to cytokines and 5azaD aloneor cytokines and sequential 5azaD and TSA following 9 days of culture retained the ability to engraft NOD/SCID mice and to generate cells belonging to multiple human hematopoietic lineages to a degree similar to primary cells (FIG. 6).

After sacrificing the mice, marrow cells from each of these groups were plated in semisolid media in the presence of human cytokines and the number of secondary hematopoietic colonies enumerated. These studies were performed in order to determine if the human transplanted grafts continued to possess the ability to generate secondary progenitor cells. Only marrow cells from mice receiving primary CD34+ cells and cultures treated with 5azaD alone or sequential 5azaD and TSA formed significant numbers of secondary hematopoietic colonies (Table 11) in vitro. The colonies were then pooled and stained with monoclonal antibodies directed against human CD45 and CD33 in order to determine if colonies were composed of human or murine cells (Table 11).

The colonies-cloned from the marrow of mice receiving sequential 5azaD and TSA-treated human grafts contained greater numbers of human hematopoietic cells than the mice receiving grafts treated with 5azaD alone. This suggests that sequential addition of 5azaD and TSA may play a role in preserving and reactivating gene expression patterns required for the maintenance of marrow repopulating potential, a functional property of HSC.

Tables Referred To In Specification

TABLE 1

Maintenance of Primitive HSC Phenotype After 9 days of Culture

| Condition | Total CD34+ % | CD34+ CD90+ % | CD34+CD133+ % | CD34+CD38- % | CD34+ CKit lo % | CD34+ Lin- ** % |
|---|---|---|---|---|---|---|
| Primary Cells | 95 | 22 | 43 | 42 | 35 | 93 |
| 5azaD & TSA 48 hr | 56 | 36 | 17 | 42 | 38 | 56 |
| 5azaD & TSA 96 hr | 63 | 31 | 19 | 42 | 48 | 63 |
| 5azaD | 30 | 7 | 12 | 20 | 19 | 30 |
| TSA | 4 | 0.8 | 0.45 | 1.8 | 3 | 4 |
| Control | 0.88 | 0.66 | 0.5 | 1 | 0.7 | 0.88 |
| 5-FU # | 27 | 1.2 | N/A | 27 | 4 | 27 |

TABLE 2

Expansion of the CD34+CD90+ Cells After 9 days of Culture

| Condition | Total counts ×10$^5$ | % CD34+ of all cells | Absolute CD34 counts ×10$^5$ | % CD34+ thy-1+ cells | Absolute CD34+ thy-1+ cells ×10$^5$ | Fold changes from the original cells |
|---|---|---|---|---|---|---|
| 5 azaD/ TSA 48 hours | 2.4 | 56 | 1.15 | 36 | 0.56 | 2.7 |
| 5 azaD TSA 96 hours | 2.1 | 63 | 1.4 | 31 | 0.71 | 3.4 |
| 5 azaD | 2.5 | 26 | 0.65 | 6 | 0.15 | 0.7 |
| TSA | 46 | 3.9 | 1.7 | o.7 | 0.31 | 1.4 |
| 5-FU | 0.025 | 26 | 0.0065 | 1 | 0.0002 | 0.001 |
| control | 64 | 0.88 | 0.56 | 0.66 | 0.14 | 0.65 |

TABLE 3

Marrow CD34+ Cells Cultured in Presence of 5azaD and TSA Retain CFC Potential

| condition | GM | BFU | Mix | Total | Clonogenic potential |
|---|---|---|---|---|---|
| 5azaD/TSA | 66 | 2 | 37 | 106 | 10.6 |
| 5azaD | 52 | 5 | 27 | 84 | 8.4 |
| TSA | 3 | 0 | 0 | 3 | 0.30 |
| Control | 7 | 0 | 0.3 | 8 | 0.76 |
| Primary cells | 54 | 59 | 13 | 126 | 12.6 |

TABLE 4

TSA Increases the number of Cycling Cells

| Condition | SG2M % 48 hours | SG2M % 72 hours |
|---|---|---|
| 5aza/TSA | 36 | 45.8 |
| 5aza | 36.5 | 35.5 |
| TSA | 36 | 41.6 |
| control | 37.4 | 29.9 |

TABLE 5

Quantitation of Hypomethylation of Marrow Cells Following 5 Days of Culture

| Condition | % Hypomethylation |
|---|---|
| Primary cells Day 0 | 10 |
| Untreated (control) | 13 |
| 5azaD/10−6M | 68 |
| 5azaD/TSA 5 ng/ml | 42 |
| TSA alone | Not Done |

TABLE 6

Enrichment of the Frequency of CAFC Following Exposure of Cells to Either 5azaD & TSA in Combination After 9 days of Culture

| Condition | CAFC/10,000 Cells |
|---|---|
| 5azaD/TSA | 82 |
| 5azaD | 96 |
| TSA | 16 |
| Control | 10 |
| Primary cells | 50 |

TABLE 7

Effects of Drug Treatments on DNA Methylation Status

| Condition[1] | % Methylation[4] | % Methylation[5] γ | % Methylation[5] ε |
|---|---|---|---|
| Primary CD34+ cells[2] | 90 | N/A | N/A |
| Cytokines[3] Alone | 87 | 100 | 100 |
| Cytokines + 5azaD | 32 | N/A | N/A |
| Cytokines + 5azaD/TSA | 58 | 70 | 67 |

Table showing the effect of drug treatment on methylation status on the -256th position of the γ-promoter region.
[1] Particular cell population studied.
[2] Primary cells are the uncultured CD34+ cells selected from human marrow.
[3] CD34+ cells were cultured for 5 days in the cytokines (IL-3, TPO, SCF and FLT-3).
[4] Each number in this column represents the calculated methylation percent by densitometry by COBRA analysis of γ-globin gene.
[5] Bisulfite sequence analysis showing the percentage methylated clones on 2 separate promoter sites of the ε and γ-globin genes.
N/A: not available.

TABLE 8

Phenotype of CD34+ Cells Prior and Following Drug Treatment

| Condition | % CD90+ | % CD117+ | % CD38− | % Lin−* |
|---|---|---|---|---|
| Primary CD34+ cells[1] | 26.0[2] ± 7.5 | 48.0 ± 6.4 | 28 ± 5.2 | 53.0 ± 16.2 |
| Cytokines + Sequential 5azaD and TSA[2] | 77.0 ± 3.7 | 65.0 ± 20.0 | 77.0 ± 5.8 | 98.0 ± 0.7 |

Table shows phenotype of CD34+ cells prior to and after exposure to 5 azaD and TSA. Each number represents the mean of 3 experiments ± the standard error of the mean.
*Lineage negative represents those cells that do not express phenotypic markers associated with terminally differentiated cells (CD2, CD14, CD15, CD16, CD19 Glycophorin A).
There is a significant increase in the percent of each marker CD90+ and CD 38− in the cytokines and sequential 5azaD and TSA treated culture when compared with the primary cells ($P < 0.01$ and $P < 0.005$ respectively, student paired t-test). There was no significant difference for CD 117+ and lineage markers.

TABLE 9

Effects of Drug Treatment on Numbers of Hematopoietic Progenitor Cells

| Condition | Total Mononuclear Cell Number (×10⁴) | Absolute CD34+ Number (×10⁴) | Absolute CD34+CD90+ Numbers (×10⁴) | Fold Expansion[2] of CD34+CD90+ |
|---|---|---|---|---|
| Cytokines Alone | 640.0[1] ± 17 | 6.0 ± 0.2 | 1.0 ± 0.4 | 0.6 ± 0.2 |
| Cytokines + 5-FU | 0.3 ± 0.0 | 0.1 ± 0.0 | 0.0 | 0.0 |
| Cytokines + 5azaD | 32.0 ± 5.0 | 10.0 ± 4.0 | 4.0 ± 1.7 | 1.7 ± 0.8 |
| Cytokines + TSA | 470.0 ± 87.0 | 19.0 ± 1.0 | 4.0 ± 1.0 | 1.8 ± 0.4 |
| Cytokines + 5azaD/TSA | 24.0 ± 4.0 | 12.0 ± 2.0 | 6.0 ± 2.0 | 2.5 ± 0.7 |

Table showing effects of drug treatment on numbers of hematopoietic progenitor cells.
[1] Each number represents the mean of 3 experiments ± the standard error of the mean.
[2] Fold change is calculated as the change in CD34+CD90+ cell numbers of the treated cells as compared to the primary cell numbers. There is a significant increase in the number of CD34+CD90+ cells between the cells exposed to sequential 5azaD and TSA and the cells exposed to cytokines alone ($P < 0.05$, paired t-test).

TABLE 10

Ability of Epigenetically Modified Cells to Form Hematopoietic Colonies

| Condition | CFU-GM | BFU-E | CFU-Mix | Total Number Colonies/plate | Plating Efficiencies[2] |
|---|---|---|---|---|---|
| Primary Cells | 52.0[1] ± 4.2 | 60.0 ± 1.8 | 10.0 ± 2.9 | 122.0 ± 4.9 | 12.2 ± 0.5 |
| Cytokines alone | 7.8 ± 1.8 | 0.0 | 0.25 ± 0.25 | 8.0 ± 2.0 | 0.8 ± 0.2 |
| Cytokines + 5azaD | 73.0 ± 0.25 | 4 ± 1.5 | 20.8 ± 9.3 | 97.8 ± 11.1 | 9.8 ± 1.1 |
| Cytokines + TSA | 13 ± 6.6 | 0.0 | 1.3 ± 0.8 | 14.3 ± 8.1 | 1.4 ± 0.8 |
| Cytokines + 5azaD/TSA | 74.0 ± 4.1 | 2.0 ± 0.0 | 21.0 ± 6.0 | 97.0 ± 2.0 | 9.7 ± 0.2 |
| Cytokines + 5-FU | 0 | 0 | 0 | 0 | 0 |

Table showing ability of epigenetically modified cells to form hematopoietic colonies.
[1]Each number represents the mean of 2 experiments ± the standard error of the mean.
[2]Plating efficiency is defined as total number of hematopoietic colonies/total cells plated × 100.
There is a significant increase in the total number of colonies when sequential addition of 5azaD and TSA are compared to cytokines alone($p < 0.01$).

TABLE 11

Hematopoeitic colonies cloned from NOD/SCID mouse marrow

| Human Grafts | % Human Cells | Estimated Number[1] of Human Colonies |
|---|---|---|
| Primary CD34+ cells | 88 | 47 |
| Cytokines Alone | 0 | 0 |
| Cytokines + 5azaD | 12 | 9 |
| Cytokines + TSA | 0 | 0 |
| Cytokines + Sequential 5azaD and TSA | 91 | 26 |

Table showing the number of colonies after plating marrow cells from mice that received human grafts 7 weeks earlier.
[1]The estimated number of human colonies is determined by the percent of human cells composing the pooled hematopoietic colonies from group of mice which stained positively with moab against CD45/CD33 antibodies using FACS analysis multiplied by the total number of colonies enumerated.

We claim

1. A method for ex vivo expansion of multipotent hematopoietic cells, comprising culturing multipotent hematopoietic cells in a medium comprising about 1 µM of an inhibitor of DNA methylation (IDM), and a histone deacetylase inhibitor (HDACI), wherein said IDM is added to said medium prior to said HDACI and wherein said IDM and HDACI are present in amounts effective to produce a composition substantially enriched in a subpopulation of multipotent hematopoietic stem cells as compared to expansion of said multipotent hematopoietic cells in the absence of said IDM and HDACI, thereby expanding said multipotent hematopoietic cells.

2. The method according to claim 1, wherein the cells to be expanded are obtained from cord blood, peripheral blood, or bone marrow.

3. The method according to claim 1, wherein the multipotent hematopoietic cells are hematopoietic progenitor and/or hematopoietic stem cells obtained by CD34 selection.

4. The method according to claim 1, wherein the multipotent hematopoietic cells are hematopoietic stem cells that retain the capacity for in vivo hematopoietic reconstitution upon transplantation.

5. The method of claim 1, wherein said IDM is 5 aza 2'neoxycytidine.

6. The method of claim 1, wherein said HDACI is TSA.

7. The method of claim 1, wherein said culture is grown in said IDM-containing medium for between about 2 to about 10 days prior to the addition of said HDACI.

8. The method of claim 1, wherein said culture is grown in said IDM-containing medium for at least 4 days prior to the addition of HDACI.

9. The method of claim 1, wherein the culture medium is changed prior to the addition of the histone deacetylase inhibitor.

10. The method of claim 1, wherein said medium comprises at least one cytokine selected from the group consisting of stem cell factor (SCF), Interleukin-1 (IL-1), Interleukin-2 (IL-2), Interleukin-3 (IL-3), Interleukin-4 (IL-4), Interleukin-5 (IL-5), Interleukin-6 (IL-6), Interleukin-7 (IL-7), Interleukin-8 (IL-8), Interleukin-9 (IL-9), Interleukin-10 (IL-10), Interleukin-11 (IL-11), Interleukin-12 (IL-12), erythropoietin (EPO), thrombopoietin (TPO), Granulocyte Colony-stimulating Growth Factor (G-CSF), Macrophage Colony-Stimulating Factor (M-CSF), Granulocyte-Macrophage Colony-Stimulating Factor (GM-CSF), Insulin-like Growth Factor-1 (IGF-1), Flt-3 ligand, and Leukemic Inhibitory Factor (LIF).

11. The method of claim 1, wherein said first medium comprises Flt-3 ligand, TPO, IL-3 and SCF.

12. The method of claim 11, wherein said cells are grown in said first medium for 48 hours and the medium is changed after 48 hours to a second medium that comprises IL-6, G-CSF, EPO, and SCF.

13. The method of claim 11, wherein said cells are grown in said first medium for 48 hours and the medium is changed after 48 hours to a second medium that comprises Flt3, TPO, and SCF.

14. The method of claim 1, wherein growth of said hematopoietic stem cells in the presence of HDACI and IDM results in at least a 3-fold increase in CD34+CD90+ cells as compared to growth in the absence of said HDACI and IDM.

15. The method of claim 1, wherein growth of said hematopoietic stem cells in the presence of HDACI and IDM results in at least a 5-fold increase in CD34+CD90+ cells as compared to growth in the absence of said HDACI and IDM.

16. The method of claim 1, wherein growth of said hematopoietic stem cells in the presence of HDACI and IDM results in at least a 10-fold increase in CD34+CD90+ cells as compared to growth in the absence of said HDACI and IDM.

17. The method according to claim 1, wherein said hematopoietic cells are separated from other cells by selecting for cells for expression of at least one marker associated with stem cells or by physical separation means.

18. The method according to claim 17 wherein the marker is selected from the group consisting of CD34, Thy-1, a lineage-specific marker and rho123.

19. The method of claim 18, wherein the marker is a lineage-specific marker selected from the group consisting of CD2, CD14, CD15, CD16, CD19, and glycophorin A.

20. A method for ex vivo expansion of multipotent hematopoietic cells, comprising culturing multipotent hematopoietic cells in a medium comprising a cytokine, an inhibitor of DNA methylation (IDM), and about 1-10 ng/ml of a histone deacetylase inhibitor (HDACI), wherein said IDM is added to said medium prior to said HDACI and wherein said IDM and HDACI are present in amounts effective to produce a composition substantially enriched in a subpopulation of multipotent hematopoietic stem cells as compared to expansion of said multipotent hematopoietic cells in the absence of said IDM and HDACI, thereby expanding said multipotent hematopoietic cells.

21. A method for ex vivo expansion of multipotent hematopoietic cells, comprising culturing multipotent hematopoietic cells in a medium comprising a cytokine, an inhibitor of DNA methylation (IDM), and a histone deacetylase inhibitor (HDAC1), wherein said IDM is added to said medium prior to said HDACI and wherein said IDM and HDACI are present in amounts effective to produce a composition substantially enriched in a subpopulation of multipotent hematopoietic stem cells as compared to expansion of said multipotent hematopoietic cells in the absence of said IDM and HDACI, thereby expanding said multipotent hematopoietic cells.

* * * * *

SEQUENCE LISTING

```
<160> NUMBER OF SEQ ID NOS: 4

<210> SEQ ID NO 1
<211> LENGTH: 30
<212> TYPE: DNA
<213> ORGANISM: Artificial sequence
<220> FEATURE:
<223> OTHER INFORMATION: Synthetic primer

<400> SEQUENCE: 1
aaaagaagtt ttggtatttt ttatgatggg                                    30

<210> SEQ ID NO 2
<211> LENGTH: 29
<212> TYPE: DNA
<213> ORGANISM: Artificial sequence
<220> FEATURE:
<223> OTHER INFORMATION: Synthetic primer

<400> SEQUENCE: 2
tcctccaaca tcttccacat tcaccttac                                     29

<210> SEQ ID NO 3
<211> LENGTH: 25
<212> TYPE: DNA
<213> ORGANISM: Artificial sequence
<220> FEATURE:
<223> OTHER INFORMATION: Synthetic primer

<400> SEQUENCE: 3
tgggagaaga aaattagtta aaggg                                         25
```

```
<210> SEQ ID NO 4
<211> LENGTH: 24
<212> TYPE: DNA
<213> ORGANISM: Artificial sequence
<220> FEATURE:
<223> OTHER INFORMATION: Synthetic primer

<400> SEQUENCE: 4
aatcaaaaca aaactaacca accc                                              24
```